(12) United States Patent
Fonash et al.

(10) Patent No.: US 7,427,526 B2
(45) Date of Patent: Sep. 23, 2008

(54) DEPOSITED THIN FILMS AND THEIR USE IN SEPARATION AND SACRIFICIAL LAYER APPLICATIONS

(75) Inventors: Stephen J. Fonash, State College, PA (US); Wook Jun Nam, State College, PA (US); Youngchul Lee, State College, PA (US); Kyuhwan Chang, State College, PA (US); Daniel J. Hayes, State College, PA (US); A. Kaan Kalkan, State College, PA (US); Sanghoon Bae, Cupertino, CA (US)

(73) Assignee: The Penn State Research Foundation, University Park, PA (US)

( * ) Notice: Subject to any disclaimer, the term of this patent is extended or adjusted under 35 U.S.C. 154(b) by 398 days.

(21) Appl. No.: 09/836,449

(22) Filed: Apr. 17, 2001

(65) Prior Publication Data

US 2002/0020053 A1 Feb. 21, 2002

Related U.S. Application Data

(60) Provisional application No. 60/201,937, filed on May 5, 2000, provisional application No. 60/197,548, filed on Apr. 17, 2000, provisional application No. 60/208,197, filed on May 31, 2000, provisional application No. 60/215,538, filed on Jun. 30, 2000, provisional application No. 60/231,626, filed on Sep. 11, 2000, provisional application No. 60/268,208, filed on Feb. 12, 2001, provisional application No. 60/235,794, filed on Sep. 27, 2000.

(51) Int. Cl.
*H01L 21/00* (2006.01)

(52) U.S. Cl. ............... 438/33; 438/50; 438/49; 438/459; 257/E21.613

(58) Field of Classification Search ............ 438/48–97, 438/455–459, 960, 33; 257/E21.613
See application file for complete search history.

(56) References Cited

U.S. PATENT DOCUMENTS 4,849,071 A 7/1989 Evans et al. ............. 156/644

(Continued)

FOREIGN PATENT DOCUMENTS

DE 198 41 430 5/2000

(Continued)

OTHER PUBLICATIONS

Kalkan et al., "Nanocrystalline Si Thin Films with arrayed void-column network deposited by high density plasma", Journal of Applied Physics, vol. 88, No. 1, Jul. 2000, pp. 555-561.*

(Continued)

*Primary Examiner*—Richard A. Booth
(74) *Attorney, Agent, or Firm*—Nixon Peabody, LLP

(57) ABSTRACT

This invention uses large surface to volume ratio materials for separation, release layer, and sacrificial material applications. The invention outlines the material concept, application designs, and fabrication methodologies. The invention is demonstrated using deposited column/void network materials as examples of large surface to volume ratio materials. In a number of the specific applications discussed, it is shown that it is advantageous to create structures on a laminate on a mother substrate and then, using the separation layer material approach, to separate this laminate from the mother substrate using the present separation scheme. It is also shown that the present materials have excellent release layer utility. In a number of applications it is also shown how the approach can be used to uniquely form cavities, channels, air-gaps, and related structures in or on various substrates. Further, it is demonstrated that it also can be possible and advantageous to combine the schemes for cavity formation with the scheme for laminate separation.

29 Claims, 13 Drawing Sheets

U.S. PATENT DOCUMENTS

| | | | |
|---|---|---|---|
| 4,881,589 A | | 11/1989 | Hartmann et al. |
| 4,995,954 A | * | 2/1991 | Guilinger et al. ............... 216/2 |
| 5,242,863 A | * | 9/1993 | Xiang-Zheng et al. ........ 438/53 |
| 5,262,000 A | * | 11/1993 | Welbourn et al. ............. 216/2 |
| 5,352,635 A | * | 10/1994 | Tu et al. ...................... 438/53 |
| 5,573,679 A | | 11/1996 | Mitchell et al. ................ 216/2 |
| 5,594,171 A | | 1/1997 | Ishida et al. |
| 5,641,709 A | | 6/1997 | Lee ................................ 438/3 |
| 5,690,753 A | | 11/1997 | Kawauchi et al. |
| 5,690,763 A | | 11/1997 | Ashmead et al. |
| 5,811,348 A | | 9/1998 | Matsushita et al. |
| 5,834,333 A | | 11/1998 | Seefeldt et al. ............... 438/52 |
| 5,854,123 A | | 12/1998 | Sato et al. |
| 5,855,801 A | | 1/1999 | Lin et al. ....................... 216/2 |
| 5,866,204 A | | 2/1999 | Robbie et al. |
| 5,880,026 A | | 3/1999 | Xing et al. |
| 5,907,765 A | | 5/1999 | Lescouzeres et al. .......... 438/49 |
| 5,925,581 A | | 7/1999 | Tolbert |
| 6,048,734 A | * | 4/2000 | Burns et al. ................. 436/180 |
| 6,057,149 A | | 5/2000 | Burns et al. |
| 6,106,913 A | | 8/2000 | Scardino et al. |
| 6,110,590 A | | 8/2000 | Zarkoob et al. |
| 6,158,824 A | | 12/2000 | Yonemura et al. |
| 6,214,701 B1 | | 4/2001 | Matsushita et al. |
| 6,225,192 B1 | | 5/2001 | Aspar et al. |
| 6,231,744 B1 | | 5/2001 | Dresselhaus et al. |
| 6,248,422 B1 | * | 6/2001 | Robbie et al. ............... 428/119 |
| 6,288,390 B1 | | 9/2001 | Siuzdak et al. .............. 250/288 |
| 6,372,608 B1 | | 4/2002 | Shimoda et al. |
| 6,399,177 B1 | | 6/2002 | Fonash et al. |
| 6,449,079 B1 | | 9/2002 | Hermann |
| 6,486,041 B2 | | 11/2002 | Henley et al. |
| 6,555,443 B1 | | 4/2003 | Artmann et al. |
| 6,774,010 B2 | | 8/2004 | Chu et al. |
| 6,905,635 B2 | | 6/2005 | Sato et al. |
| 2001/0035700 A1 | | 11/2001 | Percin et al. |
| 2002/0020053 A1 | | 2/2002 | Fonash et al. |
| 2002/0068419 A1 | | 6/2002 | Sakaguchi et al. |
| 2002/0197836 A1 | | 12/2002 | Iyer et al. |
| 2004/0005258 A1 | | 1/2004 | Fonash et al. |

FOREIGN PATENT DOCUMENTS

| | | |
|---|---|---|
| DE | 198 41 430 A1 | 5/2000 |
| EP | 0 297 258 B1 | 1/1989 |
| EP | 0 297 258 | 4/1992 |
| EP | 0 895 276 A1 | 2/1999 |
| EP | 895 276 A1 | 2/1999 |
| EP | 0 993 029 | 4/2000 |
| EP | 0 993 029 A2 | 4/2000 |
| GB | 2 258 236 A | 2/1993 |
| WO | WO 97/40385 | 10/1997 |
| WO | WO 99/27325 A2 | 6/1999 |
| WO | WO 00/74932 A1 | 12/2000 |
| WO | WO 01/75415 A2 | 10/2001 |
| WO | WO 01/80286 A2 | 10/2001 |
| WO | WO 03/050854 A2 | 6/2003 |

OTHER PUBLICATIONS

Tayanaka et al., "Thin-Film Crystalline Silicon Solar Cells Obtained by Separation of a Porous Silicon Sacrificial Layer", 2nd World Conference and Exhibition on Photovoltaic Solar Energy Conversion, Jul. 6, 1998, pp. 1272-1277.*

Kim et al. "Thin-Film Micromirror Array." *Information Display 4 &* May 1999, 30-33.

Yonehara et al. "ELTRAN; SOI-Epi Wafer by Epitaxial Layer Transfer from Pouous Si." ELTRAN Business Center, Canon, Inc., Abstract No. 438.

Stern et al. "Nanochannel fabrication for chemical sensors." *J. Vac. Sci. Technol.* 15(6), Nov./Dec. 1997, 2887-2891.

Turner et al. "Monolithic Fabrication of Nanofluidic Artificial Gel Media for DNA Electrophoresis." *SPIE* vol. 3258, 114-121.

French. "Development of surface micromachining techniques compatible with on-chip electronics." *J. Micromech. Microeng.* (1996) 197-211.

Sugiyama et al. "Micromachined sensors using polysilicon sacrificial layer etching technology." *IEDM Tech. Dig.*, (1994) 127-130.

Bell et al. "Porous silicon as a sacrificial material." *J. Micromech. Microeng.* 6 (1996) 361-369.

Steiner et al. "Using porous silicon as a sacrificial layer." *J. Micromech. Microeng.* 3 (1993) 32-36.

Boer et al. "Micromachining of buried micro channels in silicon." *J. Micromech. Systems*, vol. 9, No. 1, Mar. 2000, 94-103.

Uhlir, Jr. "Electrolytic shaping of Germanium and Silicon." *The Bell System Technical Journal.* Mar. 1956. 333-347.

Watanabe et al. "Application of a thick anode film to semiconductor devices." *Review of the Electrical Communication Laboratories.* vol. 19, No. 7-8, Jul.-Aug. 1971, 899-903.

Anderson et al. "Porous Polycrystalline Silicon: A new material for MEMS." *J. Micromech. Systems.* vol. 3, No. 1, Mar. 1994, 10-18.

International Search Report, dated Nov. 2, 2001. PCT Application No. PCT/US01/12281.

Supplementary Partial European Search Report.

Furukawa, et al. Nickel Surface Micromachining, Sixth International Symposium on Micro Machine and Human Science, 1995, pp. 161-165, IEEE.

Walter Lang, Silicon Microstructuring Technology, Materials Science and Engineering, Reports: A Review Journal R17 (1996), pp. 1-55.

Lee, et al., A novel fabrication technology for Si TFTs on flexible substrates, ECS Extended Abstract No. 791, Electrochemical Society meeting, Oct. 2000.

Wagner, et al., Flexible display enabling technology, Cockpit Displays VIII: Displays for Defense Applications, Proc. SPIE vol. 4362, p. 226-244, Sep. 2001.

Sturm, et al., Enabling Technologies for Plastic Displays, Cockpit Displays IX: Displays for Defense Applications, Proc. SPIE vol. 4712, p. 222-236, Aug. 2002.

Li, et al., Transfer approach toward fabricating poly-Si TFTs on plastic substrates ECS Extended Abstracts No. 647, Electrochemical Society meeting, Oct. 2002.

Lee, et al., High Performance Poly-Si TFTs on Plastic Substrates Using a Nano-Structured Separation Layer Approach, IEEE ELectron Device Letters, vol. 24, No. 1, Jan. 2003.

Kalkan, et al., Nanocrystalline Si Thin Films With Arrayed Void-Column Network Deposited By High Density Plasma, Journal Of Applied Physics, vol. 88, No. 1, Jul. 1, 2000, pp. 555-561.

Tayanaka, et al., Thin-Film Crystalline Silicon Solar Cells Obtained By Separation Of A Porous Silicon Sacrificial Layer, Crystalline Silicon Solar Cells And Technologies, vol. 2, Jul. 6, 1998, pp. 1272-1277.

Chou, et al., Nanoimprint lithography, J. Vac. Sci., Tech. B, 1996, 14(6), 4129-4133.

Colburn, et al., Step and Flash Imprint Lithograph, Solid State Technology, Jul. 2001.

Resnick, et al., High Resolution Templates for Steps and Flash Imprint Lithograph, J. Microlith., Microfab., Microsyst., vol. 1 No. 3, Oct. 2002.

Bender, et al., Multiple Imprinting in UV based Nanoimprint Lithography: Related Materials Issues, Microelectronic Engineering, 61-62 (2002), pp. 407-413.

Taniguchi, et al., Measurement of Adhesive Force Between Mold and Photocurable Resin in Imprint Technology, Jpn. J. Appl. Phy. vol. 41, 2002, 4194-4197.

Marsen, et al., Fullerene-Structured Nanowires of Silicon, Physical Review B, vol. 60, No. 16, Oct. 15, 1999, 593-600, The American Physical Society.

Peng, et al., Formation of Nanostructured Polymer Filaments in Nanochannels, JACS Communications, American Chemical Society, received Feb. 6, 2003.

Edited by—H. Baltes, W. Göpel, J. Hesse, Sensors Update, vol. 4, Wiley-Vch Verlag GmbH, D-69469 Weinheim, Federal Republic of Germany, 1998, 1-220.

E.I. Givargizov, Fundamental Aspects of VLS Growth, Journal of Crystal Growth, 31, 1975, 20-30, North-Holland Publishing Company.

Bjerneld, et al., Laser-Induced Growth and Deposition of Noble-Metal Nanoparticles for Surface-Enhanced Raman Scattering, Nano Letters, 2003 vol. 3., No. 5, 593-596, American Chemical Society.

H. G. Craighead, Issues In Nanotechnology Review—Nanoelectromechanical Systems, Science Mag. Nov. 24, 2000, vol. 290, 532-1535.

Fritz, et al., Translating Biomolecular Recognition into Nanomechanics, Science Magazine, Apr. 14, 2000, vol. 288, 316-318.

Wagner, et al., Vapor-Liquid-Solid Mechanism Of Single Crystal Growth, Applied Physics Letters, vol. 4, No. 5, Mar. 1, 1964, 89-90.

Michael Roukes, Nanoelectromechanical System Face The Future, Physicsweb, Feature: Feb. 2001, 1-6, http://physicsweb.org/articles/world/14/2/8/2.

Cheng, et al., Role of Electric Field on Formation of Silicon Nanowires, Journal of Applied Physics, vol. 94, No. 2, Jul. 15, 2003, 1190-1194 American Institute of Physics.

Bae et al., "Characteristics of amorphous and polycrystalline silicon films deposited at 120 C by electron cyclotron resonance-enhanced chemical vapor deposition," J. Vac. Sci. & Techol. A16(3), May/Jun. 1998, pp. 1912-1916.

* cited by examiner (a) Sacrificial layer deposition (b) Lithography and etching (c) Wall /capping layer deposition (d) Wet etchant access window etching
(Holes occur as needed in top or sides for effective etching)

(e) Sacrificial layer etching (f) Window filling

| | Substrate | | Air (empty space) | | Column/void silicon |
| --- | --- | --- | --- | --- | --- |
| | Cap layer | | Wall material | | |

Figure 5

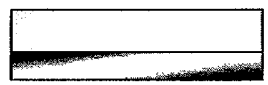 (a) Base layer deposition

 (b) Lithography and base layer etching

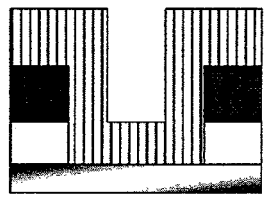 (c) Sacrificial layer deposition

 (d) Lift-off

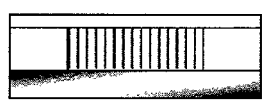 (e) Capping layer deposition

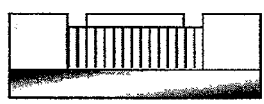 (f) Wet etchant access window etching
(Holes occur as needed in top or sides for effective etching)

 (g) Sacrificial layer etching

 (h) Window filling

 Substrate     Air (empty space)     Column/void silicon

 Stencil layer     Base/wall/cap material or materials (a) Base layer deposition
— base layer (e.g., silicon nitride)
— deposited (e.g., a-Si or poly Si)
— optimal etch stop or barrier layer
— substrate (b) Lithography and base layer etching (c) Sacrificial layer deposition (d) Lift-off (e) Capping layer deposition (f) Etchant access window etching (g) Sacrificial layer etching and trench creation (h) Window filling Figure 9
(a)
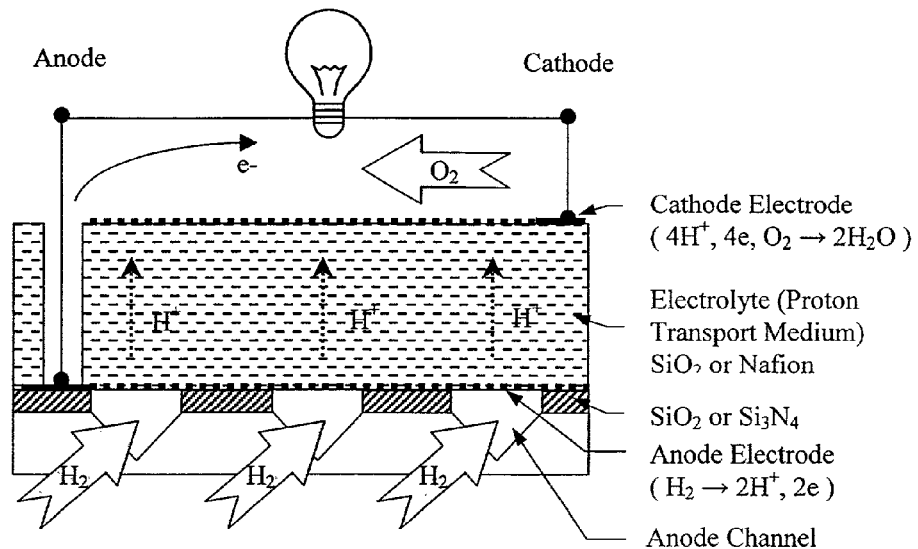
(b)
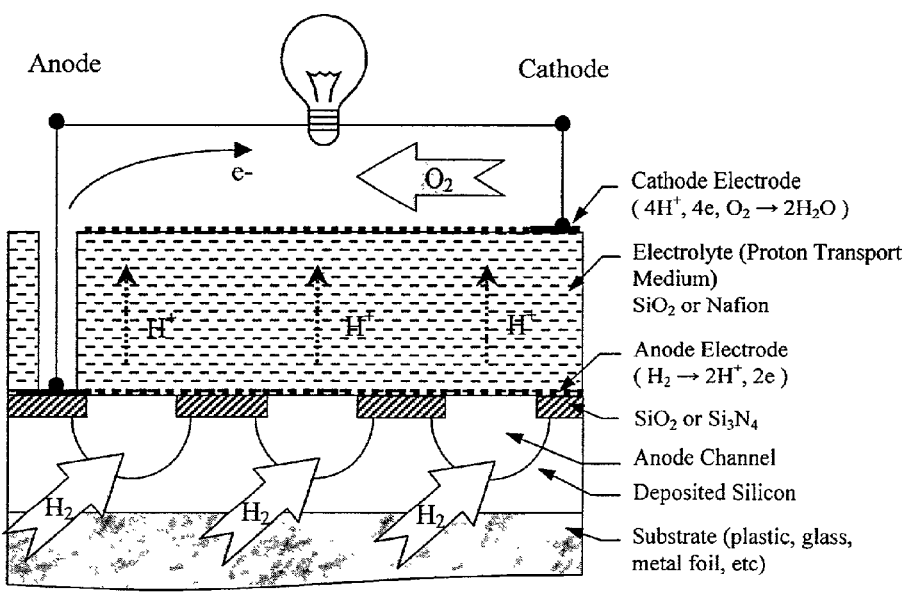

Figure 10
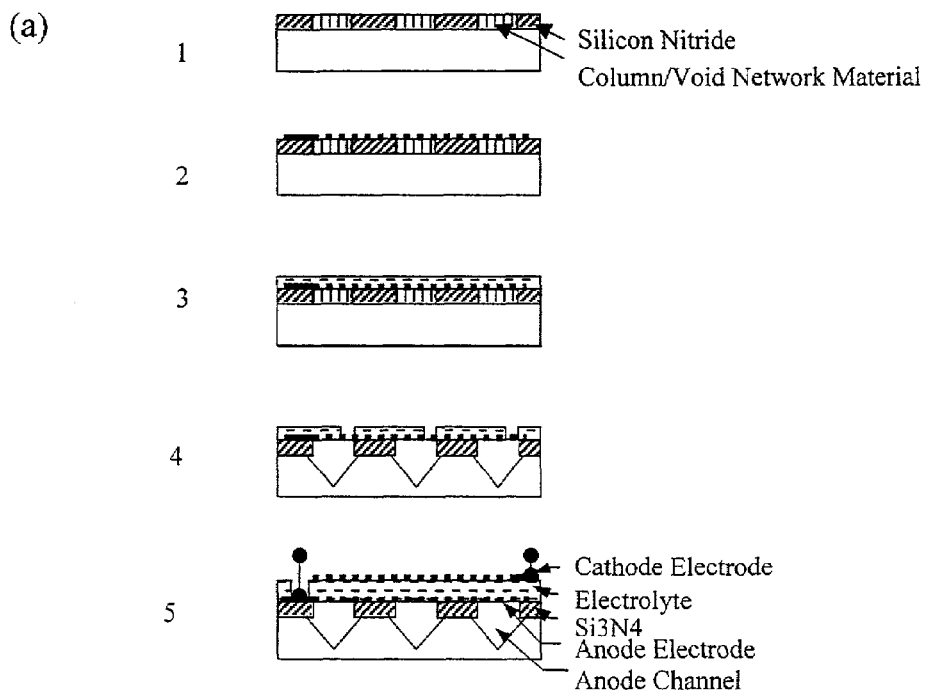
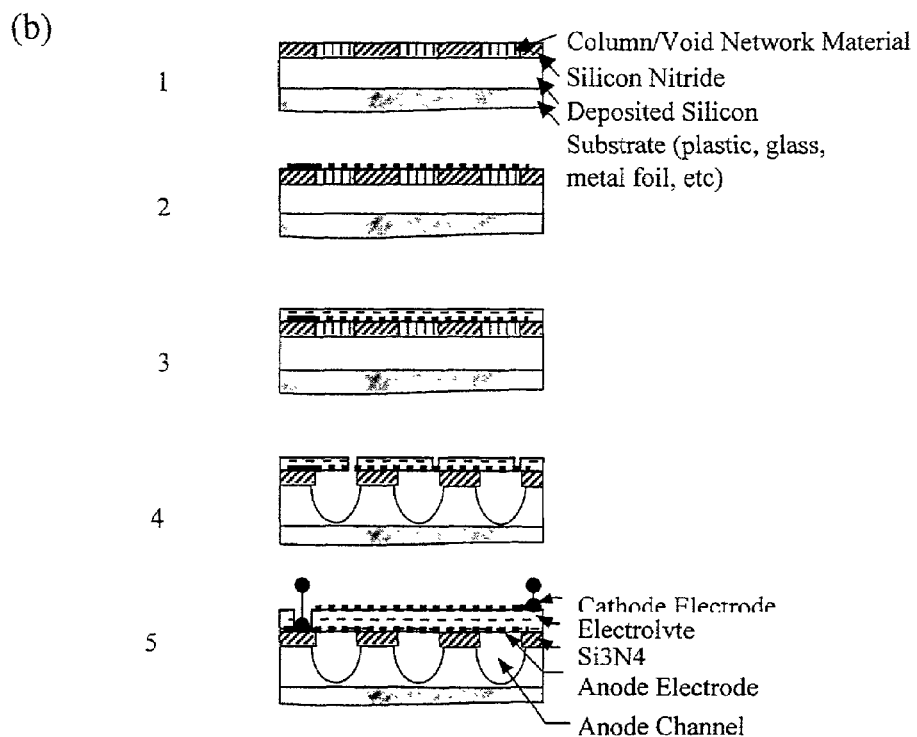

Figure 13
 (a) Cr/Au deposition
 (b) Lithography and etching
 (c) Column/void network material deposition
 (d) Contact tip etching
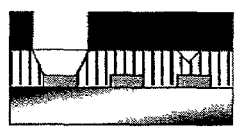 (e) Beam support etching
 (f) Lithography
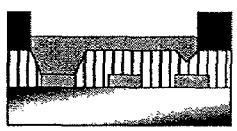 (g) Au deposition
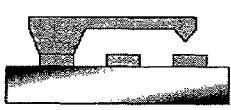 (h) Column/void network material etching

DEPOSITED THIN FILMS AND THEIR USE IN SEPARATION AND SACRIFICIAL LAYER APPLICATIONS

This application claims the benefit of U.S. Provisional Application No. 60/201,937 filed May 5, 2000; U.S. Provisional Application No. 60/197,548 filed Apr. 17, 2000; U.S. Provisional Application No. 60/208,197 filed May 31, 2000; U.S. Provisional Application No. 60/215,538 filed Jun. 30, 2000; U.S. Provisional Application No. 60/231,626 filed Sep. 11, 2000 and U.S. Provisional Application No. 60/268,208 filed Feb. 12, 2001; U.S. Provisional Application No. 60/235,794 filed Sep. 27, 2000; U.S. patent application Ser. No. 09/739,940 filed Dec. 19, 2000; now U.S. Pat. No. 6,794,196 and U.S. patent application Ser. No. 09/580,105 filed May 30, 2000, now U.S. Pat. No. 6,399,177 the contents of all are hereby incorporated by reference into this application.

U.S. Provisional Application No. 60/172,840 filed Dec. 20, 1999 claimed in U.S. patent application No. 09/739,940 was made with government support under the grant F33615-98-1-5166 415-37; 773A from the Defense Advanced Research Projects Agency. Accordingly, the U.S. Government has certain rights in the invention.

BACKGROUND OF THE INVENTION

1. Field of the Invention

The present invention is directed to deposited thin films of semiconductors and dielectrics. The present invention further relates to the use of these thin films in separation, release, and sacrificial layer applications. Separation layer and release layer applications of these thin films include functions for separating materials and structures in fabrication processing for fields such as microelectronics, displays, solar cells, sensors, detectors, opto-electronics, biotechnology, and micro-electro-mechanical (MEMs) devices and systems. Sacrificial layer applications of these thin films include sacrificial film functions for the creation of void regions for uses such as channels, tubes, "air-gaps", and cavities for microfluidics, separation/sorting structures, fuel cells, dielectrics, acoustic structures and optical structures.

2. Description of the Related Art

Separation layer approaches are used to physically separate systems of materials into at least two distinct systems. The approach is based on the use of some separation material positioned between other materials such that the separation material may be etched, mechanically abraded, or dissolved away leaving at least two, physically separated, distinct groupings of materials. Release layers are similarly used; however, in release layer applications the two materials systems are not totally separated. The separation or release layer material is often a polymer (e.g., photoresist), silicon dioxide, or polycrystalline silicon (Sang-Gook Kim and Kyu-Ho Hwang, Information Display, 15, 30 (1999). Recently, electrochemically etched porous silicon has been used as a separation layer for producing silicon on insulator (SOI) wafers for microelectronics applications (T. Yonehara and K. Sakaguchi, Abstract # 438, The Electrochemical Society, Fall Meeting, October, 2000, Phoenix, Ariz.).

Sacrificial layer approaches are used to create micro-scale and nano-scale void or cavity regions. Such voids or cavities are an enclosed empty space, which may be subsequently filled. Void creation is accomplished by removing a sacrificial material thereby leaving an empty region enclosed by an envelope of one or more materials. The size and shape of the void or cavity can be designed for the specific application. The shape may be varied and serve a variety of functions such as a channel, tube, "air-gap", or cavity. Commonly used sacrificial layer materials include polymers, silicon dioxide, and poly-crystalline silicon (M. B. Stern, M. W. Geis and J. E. Curtin, J. Vac. Sci. Technol. Vol. B15(6), pp. 2887 (1997) and S. W. Turner and H. G. Craighead, Proc. SPIE Vol.3258, pp. 114 (1998)).

Deposited or thermally grown silicon dioxide and deposited poly silicon are probably the most commonly used sacrificial materials (P. J. French, J. Micromech. Microeng. Vol. 6, pp. 197 (1996) and S. Sugiyama, O. Tabata, K. Shimaoka and R. Ashahi, IEDM Tech. Dig. pp. 127 (1994)) and their etch rate can be relatively very high when they are deposited on an open region. When used as the sacrificial layer in the creation of a void structure, such as, a channel, tube, cavity, or "airgap", these materials will, of course, be covered by a cap layer, which forms the "roof" of what will become the void region. The void or cavity region is then formed by etching away the sacrificial layer material through a window or through holes in or beside the cap layer. This window provides etchant access and reaction product exit. Consequently, the etch rate can become very low because the etch rate depends on the transport processes of the etchant solution, of the reaction products, or of both rather than just chemical reaction rate. That is, the removal of the sacrificial layer depends on the access of the etchant to and the removal of the reaction product from the sacrificial layer material as well as chemical etch rate. Consequently, materials that may have fast etch rates when deposited in open regions often have considerably slower etch rates when used as sacrificial layers.

Conventional porous silicon, produced by electrochemical etching of silicon, has also been tried for sacrificial layer application. (T. E. Bell, P. T. J. Gennissen, D. DeMunter and M Kuhl, J. Micromech. Microeng. Vol. 6, pp. 361(1996) and P. Steiner, A. Richter and W. Lang, J. Micromech. Microeng. Vol. 3, pp. 32 (1993)). However, the use of the material is hampered due to the following: its lack of uniformity and controllability, the necessity of having electrical conduction paths for the electrochemical etching required to create the material, the fact that it must be formed on a conductor, and the residual impurities left in the material after its electrochemical etching.

In general, there are a number of ways to produce void structures in addition to using sacrificial layers. All of the approaches, including the use of sacrificial layers, may be classified into two basic methods. The first, bulk micromachining, the substrate-to-substrate or wafer-to-wafer bonding technique, creates features in surfaces using standard processes such as etching, milling, embossing, stamping, etc. and then bonds a substrate and capping wafer or substrate, thereby creating nano- or microchannel features. In principle, this bonding approach is a relatively simple process. However, it requires anodic or direct (fusion) bonding and has the critical disadvantage of needing alignment of top and bottom. This makes the fabricating of small channel dimensions difficult because of misalignment of the two substrates and micro void formation at the bonding interface during the bonding process. The second technique, surface micromachining, is the method based on the use of sacrificial layers. Since it is based on sacrificial layer use, it can produce channel dimensions down to a few nanometers although to date the sacrificial layer removal step has been a relatively complex process (M. J. de Boer, W. Tjerkstra et al., J. of Microelectrochemical systems, Vol. 9, No. 1, pp. 94, March 2000). Between these techniques, surface micromachining is considered to be the most reliable method to fabricate fine structures and it certainly is the most reliable method for applications, such as optical resonate cavities, which require strict structure dimensions.

The present invention is based on using separation and release layer material and sacrificial material approaches in device fabrication. Specifically, it is based on using a new material for separation, release and sacrificial applications and a new, simple processing flow for separation layer, release layer and sacrificial layer implementation. The new materials of the present invention are deposited large material surface to material volume ratio thin films. The large surface to volume ratio insures a large empty region between material (i.e., material volume) regions allowing easy access by etching chemicals and easy reaction product removal. It insures the materials essentially wet very uniformly leading to very uniform attack and removal. In addition, the large surface area assures efficient chemical attack of the material when exposed to removing chemicals. The large surface to volume structure also leads to a mechanically weakened material for which mechanical agitation can be helpful in removal or for which gases trapped in this material may be used to enhance removal. With the materials of the present invention, procedures for separation layer applications and the removal procedure for sacrificial layer applications are more reliable than the other release and removal processes, are faster than other release and sacrificial layer approaches, and allow close process control. In addition, these novel materials are deposited and, therefore, can be used with a variety of substrates, including, but not limited to, plastics, glasses and metal foils.

SUMMARY OF THE INVENTION

The present invention is directed to a method for processing a substrate comprising the steps of (a) providing the substrate; (b) forming a high surface area to volume ratio material layer over a surface of the substrate; and (c) during subsequent processing of the substrate, removing at least a portion of the high surface area to volume ratio material layer. In an embodiment of the invention, high surface area to volume ratio material layer is deposited over the substrate in step (b). In another embodiment of the invention, the high surface area to volume ratio material layer is a columnar void layer, deposited metal, dielectric, semiconductor or organic material. The columnar void layer comprises a plurality of uniform essentially non-contacting basic columnar-like units penetrating a continuous void wherein the units have adjustable regular spacing, adjustable uniform height, and adjustable variable diameter, and the plurality of basic columnar-like units are uniformly orientated and disposed on the substrate. The basic columnar-like units are comprised of silicon, germanium, carbon, hydrogen, other inorganics, or mixture thereof. The columnar void layer has a thickness of at least 10 nm and is deposited in a vacuum environment of pressure less than atmospheric pressure at a temperature of less than about 250° C.

In an embodiment of the invention, the high surface area to volume ratio material layer is formed upon at least one intervening layer located between the high surface area to volume ratio material layer and the substrate.

In another embodiment of the invention, the removal of the high surface area to volume ratio material layer in step (c) is conducted by chemical means, physical means or a combination thereof. The removal of the high surface area to volume ratio material layer in step (c) by chemical means via dry etching, wet etching or a mixture thereof. A portion of the substrate may also removed before, while or after removing at least a portion of the high surface area to volume ratio material layer in step (c). In a further embodiment of the invention, a portion of the intervening layer between the high surface area to volume ratio material layer and the substrate is also removed.

In a further embodiment of the invention, the above described method further comprises the step of depositing at least one coating over the high surface area to volume ratio material layer after forming the high surface area to volume ratio material layer over a surface of the substrate in step (b). The coating or coatings are either organic or inorganic.

In one embodiment of the invention, the above described method further comprises the step of fabricating a device, structure or both over the at least one coating to form a device/coating structure/coating or mixture thereof. Removing of at least a portion of the high surface area to volume ratio material layer in step (c) thereby frees the device/coating structure/coating or mixture thereof from the substrate. In one preferred embodiment of the invention, the method further comprises the step of creating through-holes through the device/coating structure/coating or mixture thereof to remove the high surface area to volume ratio material layer. The through-holes can be created through the substrate, coating or coatings, or both. The method may further comprises the step of forming a second coating over the device/coating structure/coating or mixture thereof. The first coating, second coating or both act as a substrate thereby carrying the combination comprised of devices and structures, after removal of the high surface area to volume ratio material layer of step (c). In a further embodiment of the invention, after removal of the high surface area to volume ratio material layer in step (c) through the created through-holes, separating the device/coating structure/coating or mixture thereof from the substrate, thereafter further comprising the step of using the carrier substrate to dispose the separated device/coating structure/coating or mixture thereof over a second substrate.

In another embodiment of the invention, the step of removing a portion of the high surface area to volume ratio material layer in step (c) of the above described method comprises a step of selectively etching the high surface area to volume ratio material layer, such that a portion thereof is retained. The method further comprises the step of forming at least one layer over the retained portion of the high surface area to volume ratio material layer. Another further step comprises creating through-holes to access the high surface area to volume ratio material layer. Then, the step of removing the retained portion of the high surface area to volume ratio material layer uses the through-holes to produce a cavity structure. A step of depositing at least one further layer over the at least one layer, thereby blocking the through-holes may follow.

In a further embodiment of the invention, the step of providing a substrate in step (a) of the above described method comprises the step of: depositing a stencil layer on the substrate; patterning the stencil layer and selectively removing a portion of the stencil layer thereby leaving an exposed portion of the substrate and at least one retained portion of the stencil layer. The exposed portion of the substrate may be subsequently etched using the stencil layer as a mask.

The step of forming a high surface area to volume ratio material layer comprises forming the high surface area to volume ratio material layer upon the exposed surface of the substrate and on the at least one retained portion of the stencil layer, further comprising the step of lifting off the stencil layer, thereby also removing a portion of the high surface area to volume ratio material layer deposited thereon. A further step is depositing a second layer over the substrate and the high surface area to volume ratio material layer. through-holes are then created through the second layer.

After removal of the high surface area to volume ratio material layer through the created through-holes to produce a cavity structure, thereafter further comprising the step of depositing a layer that blocks the through-holes, as required. After removal of the columnar void layer in step (c) through the created through-holes to produce a cavity structure, thereafter further comprising the step of adding a gas or liquid in the cavity structure, thereafter further comprising the step of depositing a layer that blocks the through-holes and seals the cavity structure.

In one embodiment of the invention, the step of providing a substrate comprises the step of depositing a material system over the substrate; and selectively removing portions of the deposited material system retaining a portion of the material system. In a preferred embodiment of the invention, the step of forming the high surface area to volume ratio material layer over the substrate comprises the step of forming the high surface area to volume ratio material layer over the substrate and the retained material, and further comprising the step of removing a portion of the high surface area to volume ratio material layer to expose a portion of the retained material. The method further comprises the step of depositing additional material over the high surface area to volume ratio material layer and exposed portions of the previously deposited material, so that a portion the additional material contacts an exposed portion of the previously deposited material.

The present invention is also directed to a method of transferring a system of materials from a substrate comprising (a) forming a high surface area to volume ratio material layer onto a substrate; (b) forming at least one coating over the high surface area to volume ratio material layer; (c) fabricating a device, structure or both over the at least one coating to form a device/coating structure/coating or mixture thereof; and (d) removing the high surface area to volume ratio material layer thereby separating the system from the substrate. In one embodiment of the invention, the high surface area to volume ratio material layer is a columnar void layer. In another embodiment of the invention, the columnar void layer is deposited. The columnar void layer is a nano-scale composition comprising (a) a plurality of uniform essentially non-contacting basic columnar-like units penetrating a continuous void wherein the units have adjustable regular spacing, adjustable uniform height, and adjustable variable diameter, and (b) the plurality of basic columnar-like units are uniformly orientated and disposed on the substrate.

In a preferred embodiment of the invention, the first substrate is rigid. In a more preferred embodiment of the invention, the first substrate is selected from the group consisting of: silicon wafers, quartz, glass, organic materials, polymers, ceramics, semiconductors, metals, insulator materials, and mixtures thereof.

In an embodiment of the invention, forming at least one coating over the high surface area to volume ratio material layer in step (b) is performed by a technique selected from the group consisting of: deposited, applied, spin-coat, screen, printed, sputtered, evaporated, and spread. The at least one coating is organic or inorganic and is preferably a material selected from the group consisting of: chemically active materials, polymers, insulators, nitrides, oxides, piezoelectrics, ferroelectrics, metals, pyroelectrics, biological materials and semiconductors. The device is a structure selected from the group consisting of: sensors, actuators, electronics, chemical micro-fluidics, circuits, displays, optics, acoustics, solar cells, displays or opto-electronic devices, fuel cells and combinations thereof.

In one embodiment of the invention, the above described method further comprises a step of creating through-holes used to remove the high surface area to volume ratio material layer. The through-holes are created through at least a layer selected from the group consisting of: the substrate, the high surface area to volume ratio material layer, an intervening layer between the substrate and the high surface area to volume ratio material layer, layer or layers over the high surface to volume ratio material or a combination thereof; whereby creating through-holes are performed using a technique selected from a group consisting of dissolving, dry etching, wet etching, reactive ion etching, deep silicon etching, and magnetically enhanced reactive ion etching. In another embodiment of the invention, removing the high surface area to volume ratio material layer in step (d) is performed by chemical means, mechanical means or a combination thereof. In a further embodiment of the invention, the present method further comprises the step of disposing a separated device/coating structure/coating or mixture thereof over a second substrate. In another embodiment of the invention, the method further comprises the step of depositing at least one coating over the device/coating structure/coating or mixture thereof, where the at least one coating is a carrier substrate used to dispose onto a second substrate after separating the system from the substrate in step (d). In a preferred embodiment of the invention, the second substrate is flexible and an organic, glass, or metal foil material. Uses for the system over the second substrate include, but are not limited to, the fabrication of thin film transistors, electronics, sensors, actuators, acoustics, detectors, microelectro-mechanical devices, displays, fuel cells, opto-electronics or solar cells.

The present invention is further directed to a method for creating a cavity structure comprising (a) forming a high surface area to volume ratio material layer over at least a portion of a substrate;(b) forming at least one layer over the high surface area to volume ratio material layer; and (c) removing a portion of the high surface area to volume ratio material layer thereby creating a cavity structure. In one embodiment of the invention, the high surface area to volume ratio material layer deposited over the substrate in step (a) is patterned using a soft masking material, hard masking material, or a combination thereof. In another embodiment of the invention, removing the portion of the high surface area to volume ratio material layer in step (c) is performed by chemical means, physical means, mechanical means or a combination thereof. In a further embodiment of the invention, removal of the portion of the high surface area to volume ratio material layer in step (c) also removes a portion of the substrate. The one layer over the high surface area to volume ratio material layer is a material selected from the group consisting of: chemically active materials, polymers, insulators, nitrides, oxides, piezoelectrics, ferroelectrics, metals, pyroelectrics, biological materials and semiconductors. In an embodiment of the invention, gas or liquid is added into the cavity structure after the high surface area to volume ratio material layer is removed in step (c). In an embodiment of the invention, the method further comprises the step of creating through-holes through at least one layer, the substrate or both to access the high surface area to volume ratio material layer. And, the method further comprises the step of forming an additional layer over the substrate after removing the high surface area to volume ratio material layer of step (c), thereby blocking the through-holes.

In an embodiment of the invention, the height of the cavity structure is at least 10 nm, and the width of the cavity structure is at least about 10 nm.

The creation of the cavity structure provides for the fabrication of a use selected from the group consisting of: MEMS, bolometric structures, chemical reaction systems, accelerometers, display, micro-mirror formations, biomedical and medical devices, sorting, capillary functions, cell and other species studies and identification; gettering regions for solid phase crystallization or silicon on insulator structures; interlayer stress control; optical and acoustic waveguide and device applications; and fluid channels for chemical sensors; chromatography, acoustics, fuel cells and molecular sorting.

The present invention also relates to a method of creating a cavity structure in a substrate comprising (a) forming at least one stencil layer over at least a portion of a substrate; (b) removing a portion of the stencil layer thereby created an exposed portion of the substrate; (c) forming a high surface area to volume ratio material layer over the portion of the stencil layer and the exposed substrate; (d) lifting off a portion of the stencil layer, thereby also removing a portion of the high surface area to volume ratio material layer formed thereover and leaving the portion of the high surface area to volume ratio material layer formed on the exposed substrate; (e) forming at least one layer over the substrate and the high surface area to volume ratio material layer; and (f) removing the high surface area to volume ratio material layer to form a cavity structure. The stencil layer comprises a material selected from the group consisting of photoresists, nitrides, oxides, metals, polymers, dielectrics, semiconductors and mixtures thereof. The substrate is selected from the group consisting of Si wafer, quartz, glass, organic materials, polymers, ceramics, semiconductor, metals, and mixtures thereof. In an embodiment of the invention, the stencil layer in step (b) is performed using a technique selected from a group consisting of: dissolving, dry etching, wet etching, and combinations thereof. In a preferred embodiment of the invention, the lifting off the stencil layer in step (d) is performed by dissolving, etching, mechanical means or a combination thereof. In another embodiment of the invention, the method further comprises the step of creating through-holes to access the high surface area to volume ratio material layer. In a further embodiment of the invention, the method further comprises the step of adding gas or liquid into the cavity structure after the high surface area to volume ratio material layer is removed in step (f). In an embodiment of the invention, the method further comprises the step of depositing a further layer, wherein the further layer blocks the through-holes. This further layer is a material selected from the group consisting of: dielectric, polymeric, metal, photoresist, nitride, oxide, and mixtures thereof.

The present invention is also related to a method of producing at least one contact region between a first and a second material system over a substrate comprising the steps of: (a) forming a first material system over the substrate; (b) etching a portion of the first material system; (c) forming high surface area to volume ratio material layer over the first material system and the substrate; (d) removing a portion of the high surface area to volume ratio material layer to expose a portion of the first material system; (e) forming a second material system over the high surface area to volume ratio material layer and exposed portions of the first material system, so that a portion of the second material system contacts a portion of the first material system; and (f) removing the high surface area to volume ratio material layer, thereby freeing a portion between the first and second material systems while maintaining the at least one contact region. In an embodiment of the invention, the first and second material systems are selected from the group consisting of metals, semiconductors, chemically active materials, polymers, insulators, nitrides, oxides, piezoelectrics, ferroelectrics, pyroelectrics, biological materials, semiconductors and combinations thereof. The substrate is a material selected from the group consisting of: Si wafer, quartz, glass, organic materials, polymers, ceramics, semiconductor, metals, and mixtures thereof. In another embodiment of the invention, removal of the high surface area to volume ratio material layer by chemical means has an etch rate of about 25 µm per minute or less. The production of at least one contact region between a first and a second material system provides for fabrication of a structure selected from the group consisting of: MEMS devices, cantilever structures, micro-switch structures, field emission sources, micro-mirror structures, and actuators.

The present invention is further related to a method for fabricating an assembly including the step of forming channels within or over a substrate for bearing reactants, reaction products or both, the channels being formed by methods set forth above. More particularly, the method for fabricating a fuel cell comprising (a) depositing a masking layer on a substrate; (b) defining the locations of the channel regions in the masking layer; (c) covering the defined regions in the masking layer and a stencil layer in adjoining regions with a sacrificial layer material; (d) lifting off the sacrificial layer material in the stencil covered regions by dissolving or etching away the underlying stencil layer; (e) depositing anode and catalytic material over the entire resulting surface; (f) patterning this material system of step (e) to form the anode; (g) depositing an electrolyte on the resulting surface; (h) employing means to access the sacrificial layer; (i) using such means to etch or dissolve the sacrificial layer in the regions that are to be the channels; (j) using these regions of removed sacrificial material as defining regions for subsequent or continued etching or dissolving of underlying material to create the channels bearing fuel, oxidant, or both; (k) depositing and patterning the cathode and catalytic material; and (l) depositing and patterning interconnects and contacts as necessary for electrical current flow and power production.

The present invention is directed to the use of "as deposited" large surface to volume ratio materials for separation, release layer and sacrificial materials applications. In these applications, the separation, release, and sacrificial materials are removed by chemical attack, dissolution, mechanical agitation or disruption, gas pressure or chemical effects, or some combination of these. In the case of the separation layer applications, the removal of the material creates at least two, physically separated, material systems. In the case of the release layer applications, the removal of the material creates material systems that remain attached in at least one place. In the sacrificial layer applications the removal of the material creates an enclosed void or cavity (which may or may not be subsequently filled) in a materials system. The invention is demonstrated using deposited columnar void network thin films with controllable void volume as separation and sacrificial materials. These materials have a morphology that is variable and tailorable from a continuous film (no voids) to a film comprising: (a) a network of columnar-like units in a continuous void; and (b) a substrate to which the network of columnar-like units is adhered. These columnar void films can be conductors, semiconductors, or metals. They can be based on chemical elements, such as silicon, germanium, carbon, hydrogen or mixtures thereof. The films may be converted by chemical reaction into other materials such as oxides, nitrides, and inter-metallic compounds. The substrate supporting these films can be composed of various materials, including but not limited to, glass, metal, insulator material, polymeric material, semiconductor semiconductor-containing material.

As noted, the concept of large surface to volume ratio separation/sacrificial films is demonstrated in this invention using nanostructured columnar/void material with a network of units collected in clusters and formed by deposition in plasma systems. The spacing and height of the network of columnar-like units are adjustable by variables selected from the group consisting of: oxidation, silicidation, etching, voltage, current, sputtering voltage, voltage between plasma and substrate, substrate temperature, plasma power, process pressure, electromagnetic field in the vicinity of the substrate, deposition gases and flow rates, chamber conditioning, and substrate surface.

Another approach to utilizing the high performance structures that can be created on plastic laminates with the separation approach of the present invention is to dice the individual device-containing islands of the plastic or other material laminate into independent die. These can then be assembled into systems as needed using self-assembling technologies such as those based on electrostatics, chemistry, or steric compatibility.

BRIEF DESCRIPTION OF THE DRAWINGS

FIG. 1a exhibits the rigid substrate having the columnar void layer or sacrificial layer, polymer coating and device, sensor or actuator deposited thereon.

FIG. 1b shows the through-holes etched into the system.

FIG. 1c shows the removal of the columnar void layer or sacrificial layer thereby separating the device from the substrate.

FIG. 1d shows the separated device deposited onto a rugged or flexible substrate.

FIGS. 2a-d shows another approach to using separation layers and through-hole access. Structures, circuits, devices, etc. (shown here are TFTs) are fabricated on a mother substrate and then subsequently separated.

FIG. 2a exhibits the rigid substrate having the columnar void layer or sacrificial layer, polymer coating and device, sensor or actuator and an additional polymer coating on the device, sensor or actuator deposited thereon.

FIG. 2b shows the through-holes etched into the system.

FIG. 2c shows the removal of the columnar void layer or sacrificial layer thereby separating the device from the substrate.

FIG. 2d shows the separated device inverted and deposited onto a rugged or flexible substrate.

FIG. 4a shows the columnar void layer or sacrificial layer deposition on the substrate.

FIG. 4b shows the lithography and etching of the columnar void layer or sacrificial layer.

FIG. 4c shows the wall/capping layer deposited on the etched columnar void layer or sacrificial layer.

FIG. 4d shows wet etchant access window etching to produce through-holes as needed in top or sides for effective etching.

FIG. 4e etching of the columnar void layer or sacrificial layer.

FIG. 4f shows the window filling or the deposition of another coating over said void structure.

FIGS. 5a-h illustrates use of a columnar void network deposited silicon film to form an empty cross section using a deposition/etch/lift-off approach.

FIG. 5a shows the base layer deposition.

FIG. 5b shows the lithography and base layer and stencil layer etching. FIG. 5c shows the deposition of a columnar void layer or sacrificial layer.

FIG. 5d shows the lift-off process for removing the stencil layer with a portion of the sacrificial layer.

FIG. 5e shows the capping layer deposition.

FIG. 5f shows the wet etchant access window etching to produce through-holes as needed.

FIG. 5g shows the etching of the columnar void layer or sacrificial layer.

FIG. 5h shows the window filling of the void structure.

FIG. 6a shows the base layer deposition onto a substrate including substrate, optimal etch stop or barrier layer, deposited (e.g., a-Si or poly Si) and base layer (e.g., silicon nitride).

FIG. 6b shows the lithography and base layer etching.

FIG. 6c shows the columnar void layer or sacrificial layer deposition.

FIG. 6d shows the lift off of the stencil layer with a portion of the columnar void layer or sacrificial layer.

FIG. 6e shows the capping layer deposition.

FIG. 6f shows the etchant access window etching.

FIG. 6g shows the sacrificial layer etching and trench creation.

FIG. 6h shows the window filling.

FIG. 9a illustrates a fuel cell fabricated using a silicon wafer.

FIG. 9b illustrates a fuel cell fabricated using deposited silicon on a lightweight substrate such as a polymer, glass, or metal foil.

FIG. 10 illustrates a detailed fuel cell processing sequence for FIGS. 9(a) and 9(b).

FIG. 11b shows the boundary between the deep channel and shallow channel.

FIG. 11c shows an enlarged image of FIG. 11b.

FIGS. 13a-h illustrates the formation of a Release layer for application of the present material.

FIG. 13a shows the Cr/Au deposition.

FIG. 13b shows the lithography and etching.

FIG. 13c shows the column void network material deposition.

FIG. 13d shows the contact tip etching.

FIG. 13e shows the beam support etching.

FIG. 13f shows the lithography of the column void network material.

FIG. 13g shows the Au deposition.

FIG. 13h shows the column void network material etching.

DETAILED DESCRIPTION OF THE INVENTION

Figure 1:
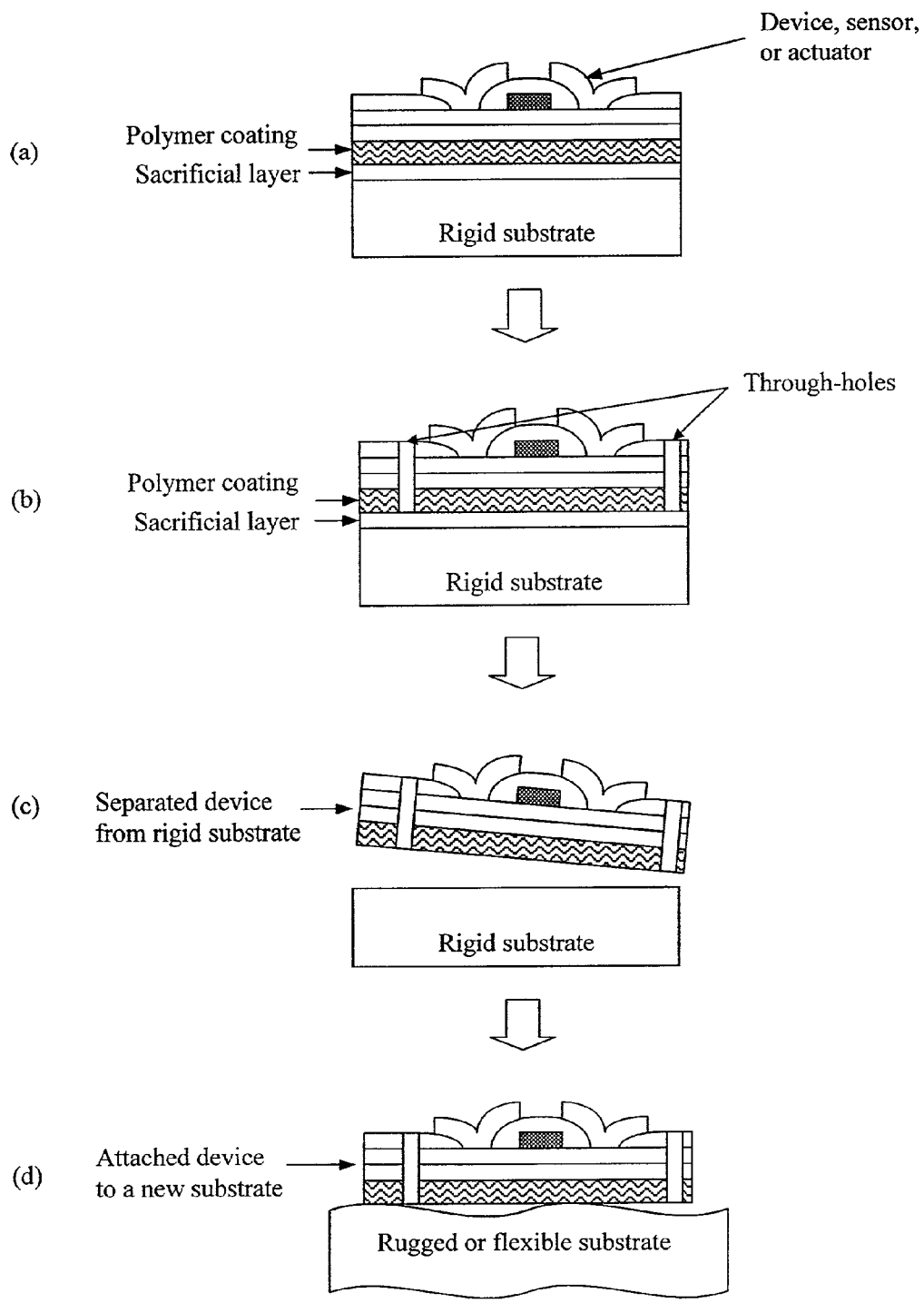
FIGS. 1a-d shows an approach to using separation layers and through-hole access. Structures, circuits, devices, etc. (shown here are TFTs) are fabricated on a mother substrate and then subsequently separated. A plastic material, deposited or formed before the device fabrication process flow, is used to provide the mechanical integrity needed after separation.

The approach to producing materials with large void volumes and therefore large surface area to volume ratios in the present invention is to use deposition to grow as-deposited porous films In the present invention, void regions (pore) are reasonably uniform through the thickness of the film and across the film. The process for deposition is unique because it is performed at low temperature, the present inventors have demonstrated that the present invention can be used to control void size and void fraction, the void-column network morphology does not vary over thicknesses of interest, the columns can be polycrystalline or amorphous material. Plasma approach including dc and rf discharge, sputtering and high density plasma tools can be used to control the interaction between deposition and etching during growth. The process, demonstrated using high density plasma deposition etching interaction, is able to give high porosity (of up to approximately 90%), controlled pore size material without any back contacts and anodization-based wet processing. Unlike other deposition processes, the present process is based on high-density plasma deposition-etching interaction and is, therefore, able to give a high degree of controllable porosity (up to 90%), a morphology that does not vary with thickness, and doped or un-doped polycrystalline columns. Also unique to the present invention is its ability to fabricate high surface to volume material on various types of substrates including glass, metal foils, insulators, plastic, and semiconductor-containing materials.

The high density plasma (HDP) deposition tool used in this demonstration was an electron cyclotron resonance plasma machine. In particular, our high surface to volume ratio columnar void network silicon was demonstrated by use of a high density plasma tool (e.g., Electron Cyclotron Resonance Plasma Enhanced Chemical Vapor Deposition (ECR-PECVD) tool (PlasmaTherm SLR-770)) using hydrogen diluted silane ($H_2$:$SiH_4$) as the precursor gas at substrate deposition temperatures less than or equal to about 250° C. This tool plays off silicon etching and deposition to create a two-dimensional silicon array and analysis has demonstrated that silicon column size is controllable, the spacing between columns is controllable, and morphology does not vary significantly with thickness. Unlike other deposited columnar silicon materials, the column spacing can be maintained as the film grows in thickness and column phase composition can be controllably varied from polycrystalline to amorphous. The resulting columnar void network structure is nanoscale in feature size and fully developed after a film thickness in the range of 10-20 nm is established. This enables the direct deposition of high surface to volume ratio of crystalline or amorphous silicon on any substrate and at any thickness greater than about 10 nm, and preferably between 10-20 nm. The high void volume semiconductor films produced by the present invention may be converted to insulators or metallic compounds through in situ or ex situ processing.

The present invention provides a deposited high surface to volume ratio film comprising a plurality of perturbations extending therefrom into a void having a porosity of up to about 90%. The plurality of perturbations are disposed substantially perpendicular to a substrate, or in the alternative, to a base layer. The plurality of perturbations are rod-like shaped columns, and may be polycrystalline or amorphous, such as a silicon material. The porosity is the result of a continuous void. The perturbations have a height adjustable by the film thickness and are of a diameter from about 1 nm to about 100 nm. More specifically, the columns have a diameter of about 3 nm to about 7 nm. Further, the perturbations are found in clusters having a diameter between about 50 to 500 nm or more.

The special attributes of the deposited columnar void network-type of high surface to volume thin films are controlled by a number of factors. These include the (a) voltage between plasma and substrate, (b) substrate temperature, (c) plasma power and process pressure, (d) magnetic field in the vicinity of the substrate, (e) deposition gases and flow rates, (f) chamber conditioning, (g) sputtering voltage, and/or (h) substrate surface. The influence of a number of these factors is not what would be expected.

The present invention further provides materials and methodologies for separating material systems into physically independent systems, for releasing materials into partially separated systems, and for creating enclosed cavities in materials. A number of applications resulting from the use of these materials and methodologies are presented. The invention uses deposited large surface area to volume ratio materials as the separation, sacrificial or release material. It is shown that particularly effective deposited large surface area to volume ratio materials are provided by deposited columnar void network films.

The present invention is demonstrated with a specific example of a deposited large surface to volume material, the deposited columnar void network silicon. This material has the large, and adjustable, surface to volume ratio (i.e., large surface area). This large surface to volume ratio means that the material has the large surface area, making it very vulnerable to chemical attack and easily mechanically weakened. The large surface to volume ratio also means that chemical species can move relatively freely through the void region penetrated by the columns. It means that the material quickly and uniformly "wets" due to capillary action leading to uniform removal procedures based on chemical attack or dissolution. Further, due to the large void volume (i.e., high porosity) of this material, it can store gases which can be used in removal processes, if gas pressure or gas interactions are used to split apart material systems in release layer applications.

There are various approaches to producing large surface to volume (i.e., large surface area) materials. The technique attracting the most attention today is based on the previously mentioned electrochemical etching. When electrochemical etching is used to produce large surface area silicon, the resulting material is commonly termed porous silicon. Porous Si was first obtained in 1956 electrochemically by Uhlir at Bell Labs but it was not until 1970 that the porous nature of the electrochemically etched Si was realized [Y. Watanabe and T. Sakai, Rev. Electron. Commun. Labs. 19, 899 (1971). Recent discussions can be found in R. C. Anderson, R. C.

Muller, and C. W. Tobias, Journal of Microelectro-mechanical System, vol. 3, 10 (1994)].

The starting material for this wet etched conventional porous Si material is either conventional silicon wafers or thin film Si produced by some deposition process such as low pressure chemical vapor deposition (LPCVD) or plasma enhanced chemical vapor deposition (PECVD). In either case, the electrochemical wet etching process requires that the silicon sample is exposed to a wet solution and a current is passed through a contact to the etching sample, through the etching sample, through the solution (e.g., a mixture of hydrofluoric acid, water and ethanol), and through an electrode contacting the solution (the cathode; e.g., platinum). This current causes the "pitting" or etching of the Si sample producing a porous network structure.

In the electrochemical (anodic) etching process the structure (e.g., pore size and spacing) and the porous-Si layer thickness are controllable by the resistivity of the silicon itself (magnitude and type), current density, applied potential, electrolyte composition, application of light, temperature, and exposure time. For sufficiently long exposures and for sufficiently thick starting material, this electrochemical etching process can be continued to the point where nanoscale structure (i.e., features of the order of nanometers) is obtained. The silicon features are a continuous single crystal when the sample is etched from a single crystal wafer, as is usually done, or polycrystalline silicon when the sample is etched from a deposited film. All these conventional (electrochemically etched) porous silicon materials are distinguished by (1) being the result of a wet, electrochemical etching process, (2) requiring a electrical contact on the sample and current flow through the sample during this wet etching, (3) having generally disconnected pore regions which can be connected after extensive etching, and (4) being the result of a sequential processing first necessitating formation of the silicon and then necessitating subsequent wet etching. Besides the complexity of having to have electrical contacts and of having to prepare, use, and dispose of wet chemical etching baths, these wet etched porous materials suffer from a problem of residual etching species and products remaining in the pores. In separation layer and sacrificial layer applications of porous silicon, one must first establish electrical contacts to, and then electrochemically etch, silicon in the region that is to become the release or sacrificial layer.

The approach to producing a high surface area to volume ratio material in the present invention is to use deposition to grow as-deposited high surface-area films. The ratio in high surface are to volume ratio materials is based on considering the excess area over and above what would be present if the film were continuous and had no voids. A preferred ratio in high surface area to volume ratio materials is up to 10,000 to 1. High surface area films are deposited films that can be placed anywhere they are needed for release layer or sacrificial layer applications. They can be deposited on planar or curved surfaces and on substrates of any composition. They can be deposited with a full spectrum of tunable, surface area to volume ratios. We have demonstrated that this tunability allows morphology from continuous (surface area is the film area; i.e., void free) films to materials with up to about 90% porosity. Due to this porosity control feature, properties such as wetability, mechanical integrity, gas content, and etch rate can be tailored, as needed. The present approach uses deposition performed at low temperature and tailored to attain the required morphology. There is no specific etching step involved and no wet processing used in preparing the material that will be the release layer or sacrificial layer. Also unique to the present invention is its ability to fabricate these deposited films, with designed morphology matched to the application, on various types of substrates including glass, metal foils, insulators, plastic, and semiconductor-containing materials including substrates with circuit structures.

The concept of as-deposited large surface to volume thin films for separation layer and sacrificial layer applications is demonstrated using columnar void network silicon material prepared by plasma enhanced chemical vapor deposition (PECVD). In particular, the present approach is demonstrated by preparing columnar void network material using a high density plasma tool (e.g., Electron Cyclotron Resonance Plasma Enhanced Chemical Vapor Deposition (ECR-PECVD) tool (PlasmaTherm SLR-770)). Deposition of the material utilized hydrogen diluted silane ($H_2$:$SiH_4$) as the precursor gas at substrate deposition temperatures less than or equal to about 250° C. The high density plasma tool approach plays off silicon etching and deposition to create a two-dimensional silicon array and analysis has demonstrated that silicon column size is controllable and the spacing between columns is controllable. The resulting columnar/void network structure is nanoscale in feature size and fully developed after a film thickness in the range of 10-20 nm is established. Columns range in diameter between 30 Å to about 100 Å. This enables the direct deposition of a large surface to volume material (i.e., high porosity material) in crystalline or amorphous phase on any substrate and at any thickness greater than about 10 nm. The columnar/void semiconductor films produced by the present invention may be converted to insulators or metallic compounds through in situ or ex situ processing. In addition, functionalizing layers may be formed or deposited after or before deposition of the columnar/void network material. By varying the deposition parameters in a high-density plasma tool, either continuous (void free) intermediate, or high void density material may be produced.

Unlike conventional porous silicon, the columnar void network silicon used in the present invention is deposited rather than formed by wet electrochemical etching thereby allowing it to be formed anywhere on any substrate. The present deposited has a unique columnar structure and contains an inherently formed void (i.e. empty space) in between the columns. That is, the morphology has the distinctive feature of being rods (columns), which are essentially perpendicular or close to perpendicular to a thin transition layer on the surface on which the film was deposited. These columns penetrate through the void. The film void is continuous facilitating fast removal of material in sacrificial, separation or release layer applications by allowing fast transport of reactants and reaction products through the layer and to and from wet-etchant, access windows or through-holes. The fast removal of the sacrificial, separation or release layer increases the reliability of the fabrication process because it reduces the possibility that other structural layers could be damaged during wet etching. In addition, the present deposited columnar void silicon can be laid down on any type of substrate, such as plastic, glass, silicon wafer and metal foil. This is another unique advantage of the deposited columnar void network silicon over conventional electrochemically wet etched porous silicon, which requires silicon substrates or films with at least one underlying electrical contact for its electrochemical formation.

I. Separation Layers

There is a great deal of interest in fabricating electronic, fluidic, solar cell, sensor and detector, chemicals and also on non-conventional flexible substrates. These substrates can be relatively inexpensive, lightweight, and flexible (e.g., plastic, glass, or metal foil) but they often have rough, uneven surfaces. In addition directly fabricating devices on such substrates can be difficult due to the difficulties of lithography and the dimensional integrity of such substrates. The electronic, chemical, display, micro-fluidic, and opto-electronic devices and structures that are advantageous to have on these substrates can comprise diodes, transistors, sensors, actuators, heat transfer systems, micro-electro-mechanical devices (MEMS), fuel cells, solar cells, and combinations of these. Fabrication of such devices and structures on non-conventional substrates offers a number of new applications because systems can be created that are foldable, shockproof, lightweight, or some combination of these. In addition the fabrication of such devices and structures on flexible substrates also allows the integration of substrates (laminates) into more complex systems, as in the example of FIG. 3, and enables the concept of Customization and Adaptability using Plastic Substrates (what we term the CAPS approach). In addition to these advantages, these new devices and circuits can be on polymer substrates such as elastomers that can be shrunk-fit to various shapes. Devices and structures on flexible substrates can be operated on curved surfaces as well as be used in harsh environments.

Figure 2:
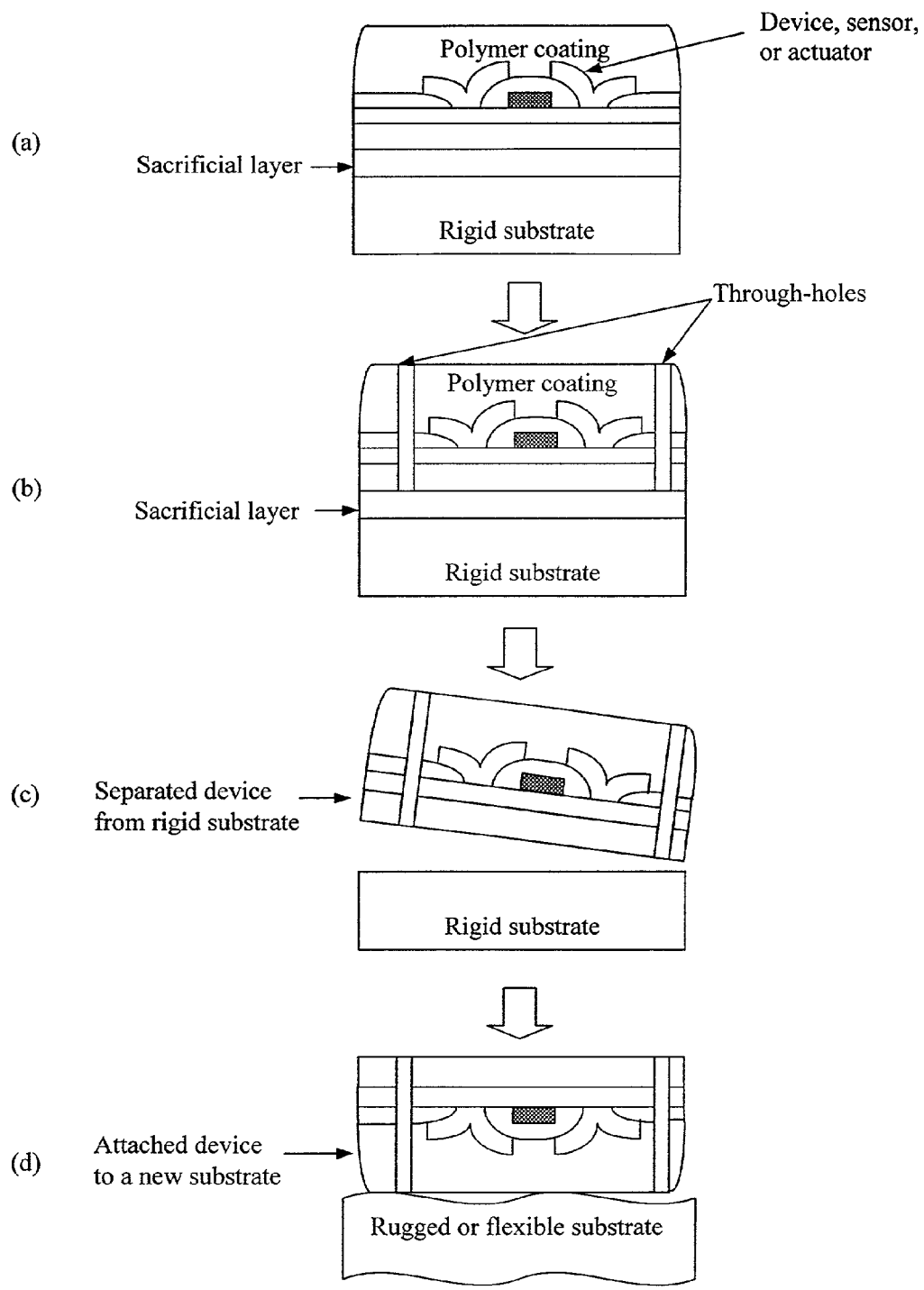
In FIG. 2, a plastic material, deposited or formed after the device fabrication process flow, is used to provide mechanical integrity after separation.

The present invention renders the fabrication of electronic, chemical, mechanical, fluidic, display, and opto-electronic devices and structures on flexible substrates into a very reproducible and manufacturable technology in spite of the rough, uneven substrate surfaces, dimensional integrity, mechanical strength, and thermal stability issues of such flexible substrates. This invention disclosed here provides the necessary separation layer materials, manufacturing technology, and applications concepts. FIGS. 1a-d and FIG. 2a-d show that there are two general approaches to using large surface area to volume ratio material as a separation layer. In both cases, structures, circuits, devices, etc. (shown here are TFTs) are fabricated on a mother substrate and then subsequently separated. In FIG. 1, a carrier substrate material such as a plastic material, deposited or formed before the device fabrication process flow, is used to provide the mechanical integrity needed after separation from the mother substrate. In FIG. 2, a carrier substrate material such as a plastic material, deposited or formed after the device fabrication process flow, is used to provide mechanical integrity after separation from the mother substrate. The latter approach offers the advantage that the processing flow may incorporate at least some high temperature steps. In either case, after separation, the plastic carrier material, for example, bearing the devices, circuits, or both may be attached to other laminates (FIG. 3), other substrates, or other objects.

In both approaches depicted in FIGS. 1a-d and FIGS. 2a-d, a conventional rigid smooth substrate such as a Si wafer, quartz, or a Corning glass substrate is chosen as the rigid mother substrate due to its having a smooth surface and compatibility with microelectronics processing. This mother substrate is intended to be reusable and may or may not have a covering layer on its surface. In the demonstration of the approach of FIGS. 1a-d and FIGS. 2a-d, we deposited a sacrificial layer onto the smooth surface of a silicon wafer, which functioned as the rigid substrate. In general, this sacrificial layer is designed to be removed by a chemical means, mechanical means, or some combination thereof. As seen in FIG. 1a, a polymer film was then coated on the sacrificial layer and this polymer coating was baked for hardening and degassing. This layer will become the transport (the carrier laminate) layer for transferring the devices and circuits to their final positioning. Subsequently, we fabricated devices on this polymer coated substrate, as shown in FIG. 1. A key step in this processing is the creation of through-holes down to the interface between polymer coating and sacrificial layer. In this demonstration we defined the location, size, and number of through-holes using lithographic techniques and etched the holes with a reactive ion etcher. These through-holes act as conduits for the chemical (e.g., acid, base or organic solution) used to remove the sacrificial layer. This chemical flows through these conduits and penetrates down to the top of sacrificial layer, wets the sacrificial layer, and chemically attacks the sacrificial layer material. In a specific experiment to demonstrate this separation technology using through-hole conduits, a metal sacrificial layer was evaporated and a 10-5 µm polymer layer was spin-coated on Corning 1737 glass. After the through-holes were defined with lithography and the holes were etched by reactive ion etching, the sample was dipped in an acid. The acid penetrates via the through-hole conduits to the top of the sacrificial layer, etching the sacrificial layer, and spreading laterally. The polymer coating is separated as the acid moves laterally and etches the sacrificial layer. As this separation process develops further, separated areas grow larger.

In a variant of FIGS. 1a-d, the through-holes for chemical access to the sacrificial layer can be in the mother substrate, which, as noted, may be reusable. By removing the sacrificial layer, the device structures and circuits on the laminate can be separated from the rigid substrate as displayed in step (c) of FIG. 1. Since the separated device structures sit on the flexible polymer transport layer, we can attach this device to any rugged-surface substrate as shown in step (d) of FIG. 1, to any surface-flat or curved, or to other laminates (See FIG. 3).

FIG. 2 displays the general features of a second version of this approach. As shown in FIG. 2, a sacrificial layer is first deposited on a rigid mother substrate prior to a device fabrication processes. This mother substrate may be reusable and may have a coating. After the fabrication of electronic, chemical, fluidic, mechanical, display, solar cell, or opto-electronic devices and structures, or some combination of these or other devices and structures, a carrier substrate such as a polymer layer is coated over the devices and structures. As seen in FIG. 2, through-holes from the polymer coating down to the sacrificial layer are created. In this demonstration, we lithographically defined the location, size, and number of through-holes using photo-lithographic process and etched the holes with a reactive ion etcher or a wet process. These through-holes provided conduits for the chemical used to remove the sacrificial layer. This chemical enters into the structure via these conduits and penetrates down to the top of sacrificial layer, wets this layer, and removes it by chemical attack. In a variant of FIG. 2, the through-holes for chemical access to the sacrificial layer can be in the mother substrate. By removing the sacrificial layer, the device structure can be separated from the rigid substrate as displayed in step (c) of FIG. 2. Since the separated device structures are covered by the carrier layer such as a flexible polymer transport layer, we can carry the laminate and attach it to any rugged-surface substrate as shown in step (d) of FIG. 2. Such laminates may be formed together to create the system seen in FIG. 3. Also the laminates can be attached to any curved surfaces.

This invention is directed to the use of general separation layers in the process outlined in FIG. 2. It is also directed to the specific use of high surface area to volume materials, such as columnar void network materials as separation layers in processes such as those outlined in FIGS. 1 and 2.

This separation process using through-hole conduits can be employed to fabricate a variety of devices and systems including thin film transistors, sensors, actuators, microelectro-mechanical devices (MEMS), fuel cells, and solar cells on the transfer (laminate) layer of FIGS. 1 and 2. Of course, the use of this sacrificial layer/through-hole and transfer layer approach can be used to establish devices and circuits on pre-existing devices, wafers, and die.

The high performance structures that can be created on plastic laminates with the separation approach can also be used in an alternative way, i.e., the structures of FIG. 1 or 2 can be formed and then the individual device-containing islands of the plastic or other material laminate can be cut, scribed, or otherwise separated into independent die. These can then be assembled into systems as needed using self-assembling technologies such as those based on electrostatics, chemistry, or steric compatibility.

Alternatively, cavities (i.e., channels) may be formed using the deposited thin film material according to the present invention by using two sacrificial layers. One of these layers is a columnar void layer and it and a second material are used in part of the region to be the channel. The other layer is some other material, such as a metal. It is the only sacrificial material in that other part of the channel. The purpose of using two materials for forming the channel is so that a very precise and very shallow channel depth in a particular region may be created where the sacrificial layers are used. That is, the shallow region can be as shallow as 10 nm in the region using the metal and the deep region in the same channel or cavity structure can be as deep as hundreds of microns in the region using both sacrificial layers. Consequently, channels with widely varying depths for sorting and sensor applications that can occur as molecules flow down the channel. In sensor application, the sensor may be placed within the shallow regions.

II. Release Layers

The release layer applications of the films according to the present invention also can have a multitude of applications. These applications are very similar to those of separation layers except the separated material systems are not completely separated and remain contacted in at least one place.

The advantages and processing of the materials of the present invention in release layer applications are similar to those of separation layers. The key difference is only that the materials systems involved in release layer applications are not completely separated and remain contacted in at least one place.

III. Sacrificial Layers

The present invention is also specifically directed to the use of as-deposited large surface to volume materials as sacrificial materials for void (i.e., cavity) creation. The void-based structures that are created have an empty space (cavity) region defined by an envelope of one or more materials. The size and shape of the cavity can be modified for the application purposes. Such structures can be used as channels applied to microfluidic applications such as in nozzle structures; in cooling or heating applications; in mimicking circulatory system capillary functions (e.g., nutrient transport, temperature control, oxygenation, etc.) for culture, tissue, and organ physical and nutrient support; in systems for drug diffusion and delivery; in nebulizers for drug delivery; in chromatography tube applications; in filtering or catalytic structures; in liquid or gas delivery systems and in reaction chambers in chemical devices such as fuel cells; and in sorting and delivery structures for bead, particle, cell, or molecule separation. These structures can also be applied to many MEMS devices such as actuators, detectors, bolometers, and cantilever sensors.

The approach to cavity (void) formation disclosed here for structures such as air-gaps, cavities, channels, and tubes is a surface micromachining technique based on the use of sacrificial layers. The patterns defining the cavity formation can be established by variety of pattern transfer approaches including conventional lithography, jet printing, beam lithography, and soft and contact printing methods. The key feature of the present new process flow is that the structures are formed using deposited large surface to volume material as the sacrificial material. The specific demonstration is done with the unique columnar void network morphology film which is an excellent large surface to volume material. For cavities, channels, etc. with cross sections that are empty or cross sections that are back filled after fabrication, the columnar void material is removed by using etchant/etch-product access holes, where the etching may be combined with mechanical agitation. If the deposited columnar void material is left in the channel (i.e., is left to occupy the cross section), such as may be useful in sorting and filtering applications, then no etching of this material is required. In this case the columnar void network material is not sacrificed but used to establish and support the void capping layer and allowed to remain.

The present inventors have discovered that the key to creating manufacturable, reproducible and controllable enclosed empty regions in materials is the deposited large surface to volume material approach. The present invention demonstrate this approach using columnar void network silicon, which, unlike conventional porous silicon, is deposited, involves no electrochemical etching, and has a unique, regular and controllable columnar void morphology wherein the silicon penetrates the void. Using plasma deposition processes at low temperatures allows the material to be laid down on a wide variety of substrates including previously formed circuits and devices, plastics, glass, organic and polymeric materials, and metal foils. Its columnar void structure makes it a filter medium in filled channel applications or an excellent precursor for the creation of empty channels, voids, cavities, and tubes in empty cross section applications. In the latter case, it is a sacrificial layer and, as such, gives a fast etch rate even when etched through small sized, wet-etchant access windows. The open region of the columnar void network silicon film allows fast transport of the etchant and reaction products in sacrificial layer removal and the fast sacrificial etch rate increases overall process reliability. In addition, the fast etch rate allows the making of fine structures with thin capping layers. The bottom, side-walls, and top of the channels formed by this approach can be comprised of a variety of organic and inorganic materials including elastomers, insulators, semiconductors or metals. They can be comprised of active layers such as those encompassing current carrying structures, gate structures, piezoelectrics, pyroelectrics, ferroelectrics or magnetic materials. The bottom, side-walls, and top of the channels, voids, cavities, air-gaps and tubes can also be comprised of materials such as small organic molecules, or polymers. The sacrificial layer use can be employed in deposition/etching formation approaches (FIGS. 4a-f), in deposition/etching/lift-off formation approaches (FIGS. 5a-h), or combinations thereof.

Normally, when lift-off processing is used, the key to a successful process is to insure that the thickness of the deposited film to be lifted off should be much thinner than the stencil layer at the sides of the step pattern (see FIGS. 5a-h), or to insure this film to be lifted-off should be discontinuous. Therefore, lift-off processes are often not used in the fabrication of MEMS or bioMEMS devices, since these can require relatively thick films. However, the deposited columnar void silicon of the present invention has a very unique continuous void (silicon columns penetrating the void from a transition layer) morphology and this morphology allows easy access of gases and liquids to the stencil layer (the layer causing the lifting-off) for chemicals designed to remove this layer. For example, if the stencil layer is photoresist, then we find acetone is able to readily attack the photoresist located under even thick columnar void silicon layers. In this case, acetone travels through the void region penetrated by the silicon columns and reaches the photoresist (stencil) layer, dissolves the layer, and lifts-off the silicon film that resided on the stencil. Because of the unique columnar void morphology of the particular silicon material, this lift-off approach works even for thick deposited columnar void network Si films.

As noted, with the nano- or micro- voids, cavities, channels, etc. can be fabricated either by some variant of deposition/etching processing (FIGS. 4a-f) or they can be fabricated by some variant of very advantageous deposition/etching/lift-off processing (FIGS. 5a-h). In either case the fabrication can involve only low temperature processes and has flexible design rules. The deposition/etching/lift-off processing is especially advantageous since it also offers very simplistic processing, super flat surfaces, and thin capping layers. Both deposition/etching processing (FIGS. 4a-f) or deposition/etching/lift-off processing (FIGS. 5a-h) can be applied to a wide range of substrates including organics, plastics, glass, deposited semiconductors, semiconductors with previously fabricated circuits and chips, silicon chips or wafers, and metal foils. It is to be noted that these substrates can be curved, either prior to or after fabrication.

The flat surfaces and the thin capping layer structures (e.g., channels for fluid flow) possible with the lift-off approach are advantageous to cooling or heating applications because the flat surface and thin capping layer increase heat transfer efficiency by increasing the interface area in contact with whatever is to be heated or cooled. Since the channels can be fabricated with low temperature, non-destructive processes in the methodologies, the present approach allows cooling (or heating) structures to be built directly onto circuits and devices after their fabrication. Since the channels of the present invention can be fabricated on metal or plastic foils, heat sinking channel-based structures, for example, can be fabricated on foil substrates such as the laminates of FIG. 3 and then adhered onto circuit and device structures for cooling and temperature control.

The flexible design rules permitted by the present approach also allow applying the voids, cavities, channels, etc. to a wide range of other nano- or micro fluidic applications such as nozzles; mimicking circulatory system capillary functions (e.g., nutrient transport, temperature control, oxygenation, etc.) for culture, tissue, and organ support; capillary systems for drug diffusion and delivery; nebulizers for drug delivery; tubes for chromatography and fuel cells; filtering or catalytic structures; and sorting structures for bead, particle, cell, or molecule separation. In addition channels can function as scaffolds as well as capillaries for cell, tissue, and organ growth.

A detailed discussion of an example of the process flow involved in the deposition/etching approach to fabricating nano- and micro- void structures can be undertaken using FIGS. 4a-f. In the demonstration of the structure of FIGS. 4a-f, silicon dioxide first was actually deposited as a coating layer (not shown in FIGS. 4a-f) on the substrate using a Plasma Therm SRL770 electron cyclotron resonance-plasma enhanced chemical vapor deposition (ECR-PECVD). The detailed deposition conditions are described in Table 1. The silicon dioxide was used as a bottom layer for the void structure, and it (or other layers that may be used for the same function) can be used to prevent any possible substrate etching when the columnar void network silicon release layer is being removed, i.e., such materials can be used as etch stop layers. In the case of the processing used in the demonstration of the process flow of FIG. 4, the etchant used to remove the deposited columnar void network silicon was tetra methyl ammonium hydroxide (TMAH). The etch selectivity of TMAH to etching deposited columnar void network silicon over silicon oxide is very high, and the 500 Å of silicon dioxide used in this demonstration was thick enough to protect the substrate. Another purpose of silicon dioxide (or other first layer) deposition can be to act as an interdiffusion barrier layer and to improve the interface with the substrate being used. The latter can be very important, for example, for stress control Micro- and nano-cavities, made with the present approach, can also be used for dielectric isolation and for the tailoring of optical response and interactions. For example, they can be applied to the intermetal dielectric (IMD) microelectronic chip applications and optical device applications such as anti-reflection and absorption structures, optical switches, waveguides, and amplifiers. For optical applications the fundamental optical frequency of cavities can be tuned by changing cavity size and shape, and surrounding material refractive index, and this ability to tune the resonant mode is very useful for the optical devices such as tunable optical filters, optical gates, optical switches, channel drop filters, and optical interconnects. Low dielectric constant (i.e., low k) applications can require multiple cavities, and wider sizes of cavity structures than optical applications because the structures have to provide a low dielectric constant yet have mechanical stability.

The columnar void network silicon layer was the next layer to be deposited in this demonstration. It was deposited after ECR-PECVD chamber conditioning using hydrogen plasma and oxygen plasma runs. Such conditioning can be useful for process control for release, separation, or sacrificial layer deposition. The detailed chamber conditioning parameters that were used in this demonstration are described in the Table 2. The conditioning using hydrogen plasma and oxygen plasma was performed for 30 min and 10 min., respectively. The columnar void network silicon, to be used as the sacrificial layer, was then deposited by the same ECR-PECVD. Since this columnar void network deposited silicon layer will be removed by a subsequent etching process (in this demonstration TMAH wet etching was used) to create the cavity region, this silicon deposition dictates what space will be the cavity region for the airgap, channel, etc. As seen in the drawing of FIGS. 4a-f, the thickness of the deposited columnar void network silicon is the height dimension of the cavity in this approach; consequently, the height of the cavity region can be changed very easily and accurately. Alternatively, another material may be deposited before the columnar void network silicon and it too may be designed to etch when the columnar void material etches giving a deeper final cavity (for a channel, airgap, etc.) whose depth is not controlled by the columnar void silicon thickness. An example of such a void (cavity) is seen in FIGS. 6a-h; in this case the processing approach of FIGS. 5a-h was followed but that of FIG. 4 also may be used.

Returning to FIGS. 4a-f, after completion of the deposition of the columnar void network silicon layer, another 500 Å of silicon dioxide layer was deposited on the silicon layer in this example. This was done because the columnar void network silicon is extremely mechanically fragile because of the huge pore volume possible due to its morphology of columns penetrating a continuous void. The columnar void network silicon can be damaged even by the developers and photo resist removers used in lithography processes, if such a covering layer is not used.

Figure 4:
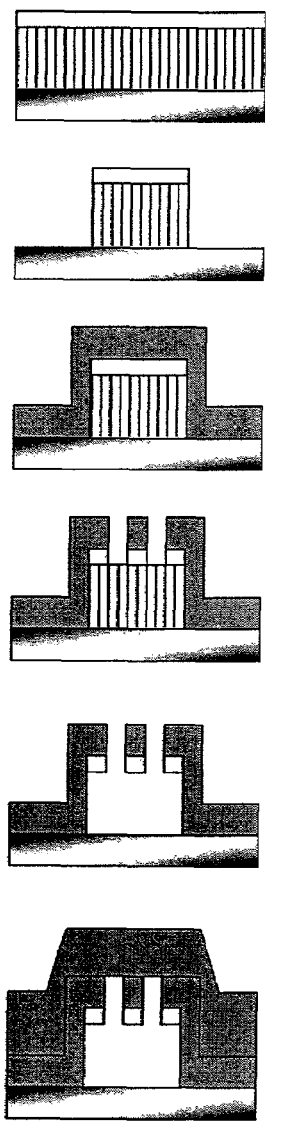
FIGS. 4a-f illustrates use of a columnar void network deposited silicon film to form an empty cross section using a deposition/etch approach.

In this demonstration of the present invention of using deposited columnar void network silicon to create void (i.e., cavity, channel, airgap, etc.) structures, the three layer sandwich present after the previously described three depositions was next patterned using lithography and etching to give the structures seen in step b of FIG. 4. These were then coated by silicon nitride where this capping layer was deposited by ECR-PECVD. Silicon nitride serves as the pillars and capping (roof) layer in this particular experiment. The detailed deposition parameters are shown in Table 1. In the demonstration shown, 1000 Å of silicon nitride was deposited on the top of the three layers and on the sidewalls and bottom of the holes. It was very conformal. The thickness of the silicon nitride layer could be adjusted to modify properties such as strength, dielectric constant, optical properties, diffusion barrier properties, thermal conductivity, or some combination of these. Other coating materials may be used and similarly adjusted. Alternatively lift-off processes may be used to form the deposited porous silicon region and only a capping role would then be played by this layer.

Small window structures are required in, or adjacent to, the cap layer to etch out the deposited columnar void network silicon sacrificial layer, as seen in FIG. 4d. In this demonstration these were established using a lithography process performed using Shipley 1813 photoresist. After the lithography processes, the window patterns were etched by Plasma Therm 720 Reactive Ion Etching (RIE) system. $CF_4/O_2$ plasma was used and the detail etching parameters were described in Table 3.

TABLE 1

ECR-PECVD deposition parameters

|  | Silicon dioxide | Columnar void network Si | Silicon nitride |
| --- | --- | --- | --- |
| RF power (W) | 900 | 500 | 900 |
| Process Pressure (mtorr) | 4 | 8 | 4 |
| Substrate Temp (° C.) | 300 | 100 | 300 |
| Process Gas/Flow Rate (sccm) | $SiH_4$/4 $O_2$/5.1 Ar/3 | $SiH_4$/2 $H_2$/40 | $SiH_4$/4 $N_2$/5 Ar/3 |
| Deposition time (min) | 3.47 | 30 | 12.20 |

TABLE 2

Chamber conditioning parameters

|  | Hydrogen plasma | Oxygen plasma |
| --- | --- | --- |
| RF Power (W) | 800 | 800 |
| Process pressure (mtorr) | 5.5 | 4 |
| Substrate Temp (° C.) | 300 | 300 |
| Process Gas/Flow Rate (sccm) | Ar/3 $H_2$/20 | Ar/3 $O_2$/18 |
| Deposition Time (min) | 30 | 10 |

TABLE 3

RIE etching parameters

| DC Power (W) | 400 |
| --- | --- |
| Process Pressure (mtorr) | 200 |
| Substrate Temp. (° C.) | 25 |
| Etching time (min) | 1.10 |
| Etching Gas/Flow Rate (sccm) | $CF_4$/45 $O_2$/5 |

Nanostrip removed the photoresist used to define the RIE step by dipping the samples in the solution for 10 minutes. Next a 0.1% solution of BOE (Buffered Oxide Etcher) followed to remove the native oxide layer on the columnar void network silicon surface exposed by the windows. The BOE process was a very important step because it could damage other structural layers. Therefore, the BOE etching time and the concentration of the solution were very important in this particular demonstration.

Figure 7:
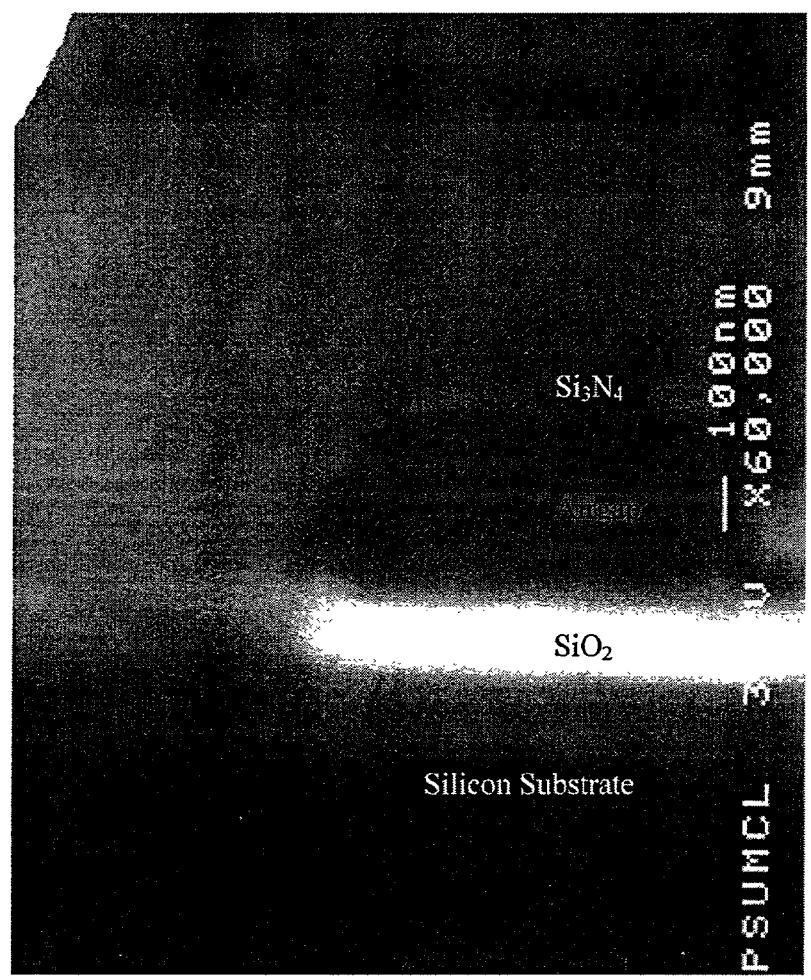
FIG. 7 is a cross-sectional SEM micrograph of a void or cavity structure fabricated following the deposition/etch approach outlined in FIG. 4.

With the etchant/reaction product windows in place, the deposited columnar void network silicon sacrificial layer was removed by TMAH solution. For the void (cavity region) of this demonstration the columnar void network silicon sacrificial layer removal took less than 30 minutes to complete, as compared to conventional release layer processes which can take upwards of 20 hours. The rinse and dry processes following etching removal of the release layer were important process steps because the structure became very fragile after etching the release layer. Rinsing was accomplished by immersion of the samples into DI water with constantly flowing, additional DI water entering the bath. The samples were rinsed more than one hour, and dried by very weak nitrogen blow dry. The angle of the nitrogen flow was also very important and the blowing direction was almost parallel to the sample surface. It was found that vacuum chamber environment drying was very effective and it was the least damaging process to the sample. The result of this demonstration of the approach of FIG. 4 is the void structure shown in FIG. 7. The structure of the void-column deposited porous silicon consists of an array of columns in a continuous void (pore); hence, it is a void column network material.

A detailed discussion of an example of the very advantageous deposition/etching/lift-off approach according to the present invention can be undertaken using the method set forth in FIG. 5. In the actual processing demonstration following this procedure Corning 1737 glass was used as the substrate. Acetone, IPA and DI water were used to clean this substrate for 20 minutes in an ultrasonic bath. Next 5000 Å of silicon nitride was deposited on the cleaned substrate using electron cyclotron resonance-plasma enhanced chemical vapor deposition (ECR-PECVD) after the substrate was baked on a hotplate for 10 minutes to remove DI water vapor. The detail deposition conditions of the silicon nitride, which serves to define the bottom of the channel in this example, are shown in Table 4. Shipley 1813 photoresist was used for the first lithography process (i.e., to pattern the nitride) and this pattern was used again for the lift-off process. The characteristics of the photoresist were a crucial factor for the lift-off process because, if the photoresist was exposed to a high ion energy plasma for a long time, it could be hardened and could be difficult to remove using acetone cleaning even in an ultrasonic bath. Most of the columnar void silicon film deposited on the stencil (here the photoresist) lifted off within a minute of immersion in this bath, and the process was completed after 3 minutes. The lift-off process provided super flat surfaces without chemical mechanical polishing (CMP) processing, and it allowed the option of a thin capping layer keeping the flat surface and it allowed multiple layers of tubes or cavity structures with crossovers. The substrate was cleaned using acetone, isopropylalcohol and deionized water after lift-off, and baked on the hot plate for 10 minutes. Next 2000 Å of silicon nitride was deposted on top of the substrate as a capping layer. The deposition condition was the same as the first silicon nitride layer and the deposition rate was calculated from the first silicon nitride layer deposition. The $Si_3N_4$ was etched at 200W and 50 G for 160 seconds, and $CF_4$ and $O_2$ are used as process gases in the demonstration. One lithograph step could be used to define both the channel bottom and the stencil layer, if, for example, the photoresist served as the defining layer for the nitride etch and as the stencil. The nitride was etched with reactive ion etching (RIE) using $CF_4/O_2$ mixed gases under conditions in the Table 5. The silicon nitride layer was over-etched to make sure of the removal of the layer. In this example the photoresist mask for this nitride bottom definition etching was not used as the stencil for lift-off. Instead it was removed using acetone even though the same photoresist layer pattern was required for the following lift-off process. There were two reasons for the photoresist removal used in this particular example. The first one is that, for the etch parameters and materials used in this example, the photoresist used as the nitride mask was hardened due the etch plasma exposure and was difficult to remove making it a poor candidate for a lift-off process. Secondly, for the etch parameters and materials used, there was a thickness change in the photoresist in this example processing due to the plasma exposure. This could be a factor that might lead to failure of the following lift-off process; hence, the nitride mask photoresist was removed after nitride etching to obviate these two factors. A second photoresist and exposure was done to form the stencil. Alternatively parameters or materials could be changed to eliminate the need for this second photoresist application and exposure. For example, a thicker photoresist serving as both the nitride etch mask and stencil could have been used to remove the need for this double lithography process employed in the present demonstration. Alternatively non-polymeric materials could be used as the stencil for lift-off.

After creation of the stencil, a columnar/void network type silicon was deposited using the same ECR-PECVD that was used for silicon nitride deposition, and the detailed deposition parameters are described in Table 4. Subsequently, lift-off was done in an ultrasonic acetone bath. Most of the columnar void silicon film deposited on the stencil (here the photoresist) lifted off within a minute of immersion in this bath, and the process was completed after 3 minutes. The lift-off process provided super flat surfaces without chemical mechanical polishing (CMP) processing, and it allowed the option of a thin capping layer keeping the flat surface, multiple layers of tube or cavity structure with crossovers. The substrate was cleaned using acetone, IPA and DI water after lift-off, and baked on the hotplate for 10 minutes. Next 2000 Å of silicon nitride was deposited on top of the substrate as a capping layer. The deposition condition was the same as the first silicon nitride layer and the deposition rate was calculated from the first silicon nitride layer deposition.

An additional lithography step was then performed to make widows (access holes for the chemical to be used to attack the sacrificial material) at predetermined locations to allow wet etchant access to the columnar void film. RIE was used for the etching of these spaced windows. The etching condition was also the same as the previous one, and the etch time was also calculated from the first silicon nitride etch rate. The substrate was immersed to the 1% BOE for 2 minutes to remove any oxide layer that may have grown on the columnar void silicon surface before the sacrificial layer etching. Then 5% tetramethyl ammonium hydroxide (TMAH) was used to do the etching, through the access holes, of the sacrificial layer columnar void silicon. This TMAH solution was heated at 75° C. The etched samples were subsequently cleaned in flowing DI water for 30 minutes, and dried in a vacuum environment.

The access windows were sealed (see FIG. 5) by use of a spin on glass (SOG), and the thickness of the SOG film could be tuned by changing the spin speed of the chuck. The sample was cured on a hotplate. These access hole windows may be left unfilled, if advantageous in applications such as nutrient delivery, drug delivery, nebulization.

TABLE 4

ECR-PECVD deposition parameters

|  | Columnar void network Si | Silicon nitride |
|---|---|---|
| RF power (W) | 500 | 900 |
| Process Pressure (mtorr) | 8 | 4 |
| Substrate Temp (° C.) | 100 | 100 |
| Process Gas/Flow Rate (sccm) | $SiH_4/2$ $H_2/40$ | $SiH_4/10.7$ $N_2/8$ $Ar/3$ |
| Deposition time for 5000 Å (min) | 30 | 30 |

TABLE 5

RIE etching parameters

| DC Power (W) | 200 |
|---|---|
| Process Pressure (mtorr) | 200 |
| Substrate Temp. (° C.) | 25 |
| Etching time for 5000 Å (min) | 1 |
| Etching Gas/Flow Rate (sccm) | $CF_4/45$ $O_2/5$ |

Figure 8:
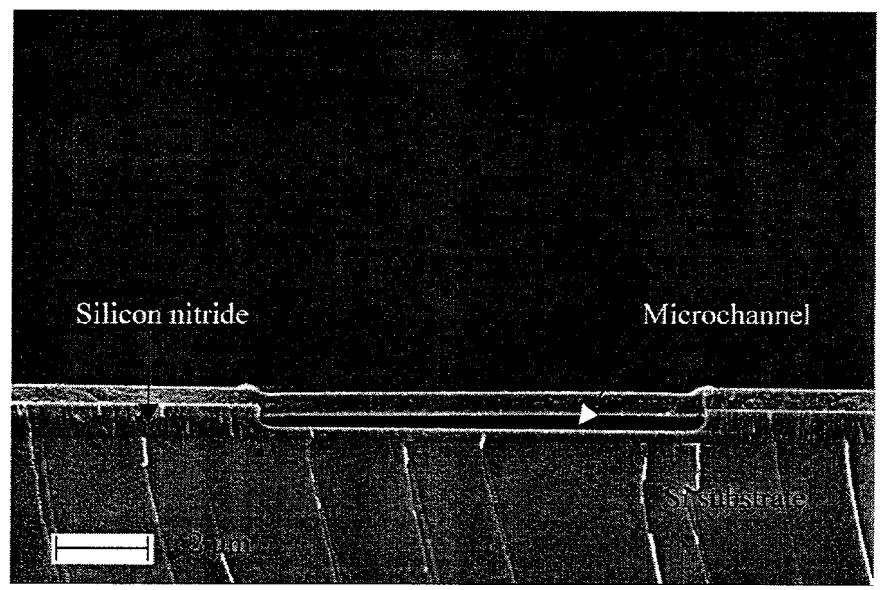
FIG. 8 is a cross-sectional SEM micrograph of a void or cavity structure fabricated following the deposition/etch/lift-off approach outlined in FIG. 5.

A cavity structure fabricated following the processing flow concepts outlined in FIG. 5 is shown in FIG. 8 FIG. 8 shows a micro tube. The width of this tube is in the range of about less than 100 μm and preferably between 10 μm and 501 μm, and has a base layer under the tube structure. The height of the tubes range between 0.5 μm and 50 μm and may be as low as 50 nm. Since a silicon wafer was used as the substrate, the base layer $Si_3N_4$ was used for the tube to prevent substrate etching during the sacrificial layer etching process. Capping layers used for these tubes were 5000 Å in thickness. This thickness is seen to be too thin for the 50 μm wide tube, which is seen to have some cap layer bending in the middle. The bending is caused by the bubbles produced during the sacrificial layer etching. This bending increases as the width of the tube increases. For example, for the 5000 Å capping film, the height of the bend is about 1.5 μm. This is about three times higher than the original tube height. The fast etch rate of this columnar void network material prevents thinning or damaging of the other structural materials and allows the fabrication of up to 100 μm wide tubes. For tubes more than 100 μm in width, a 5000 Å capping layer results in a cracked tube ceiling and ceiling collapse due to stress from the capping layer bending. The thicker capping layer can improve the capping layer bending problem and allow the fabrication of wider widths to tubes.

A thicker capping layer can allow the fabrication of wider widths of tubes, and modifying the design for and placement of the access holes can be another factor in allowing tube structures, wider than 100 μm.

There are applications such as sorting and filtering for which there may be advantageous to leaving the columnar void network in the cavity, channel, airgap, etc and not remove it. This could be done in either the process flow outlined in FIG. 4 or 5 or some variant or combination of these.

Figure 6:
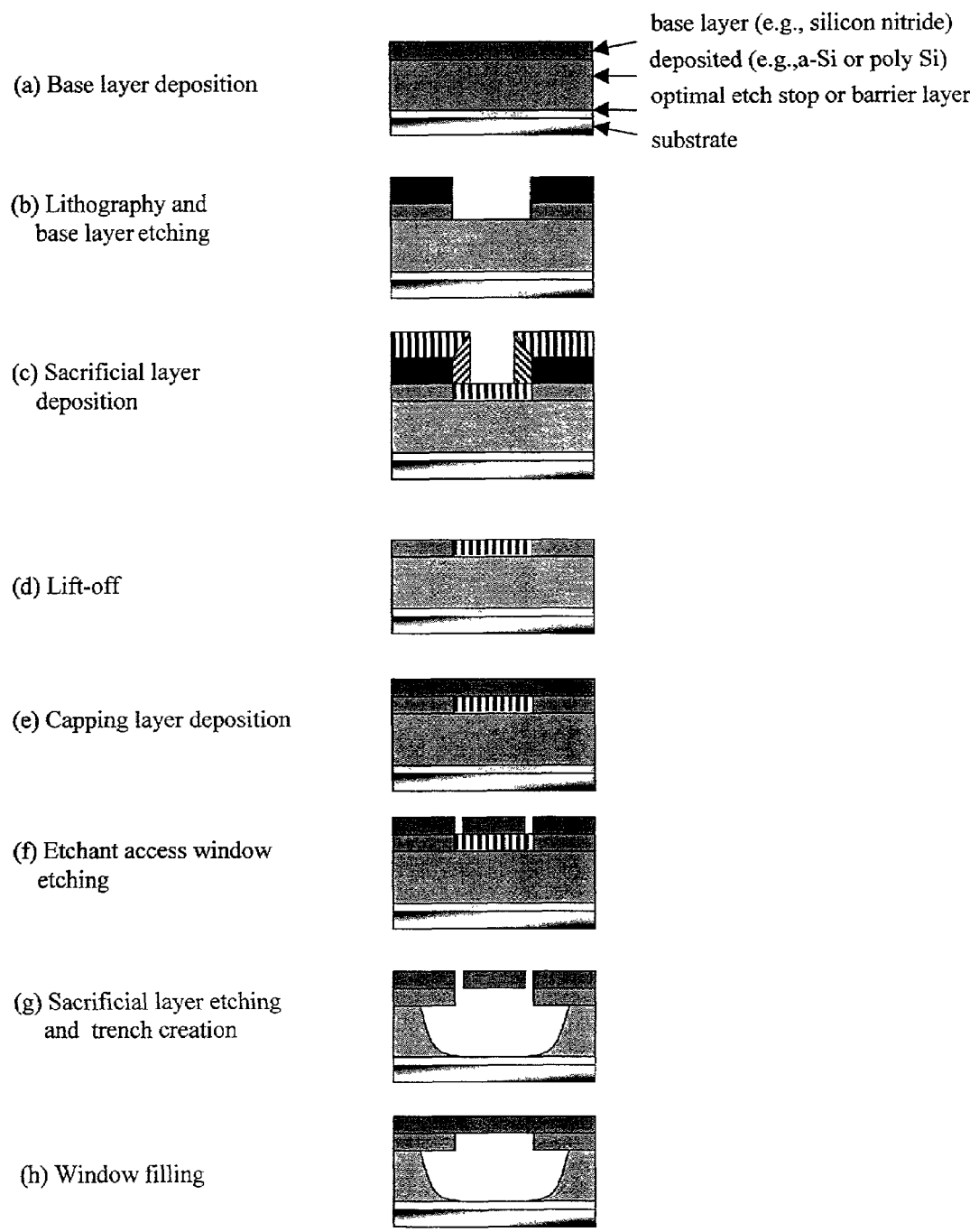
FIGS. 6a-h illustrates use of a columnar void network deposited silicon film to form an enclosed empty structures such as channels, tubes, cavities, etc. of relatively large cross-section that can be fabricated with simple wet chemical etching without the need for the so-called, deep-etch reactive ion etching process.

The use of large surface to volume ratio materials as sacrificial materials allows a deposition/etch approach or a deposition/etch/lift-off approach to sacrificial material removal. The deposition/etch approach is shown schematically in FIG. 4; the deposition/etch/lift-off approach is shown schematically in FIG. 5. In the demonstrations of the present invention, both approaches used in conjunction with the columnar void network silicon deposited films. The lift-off based approach, which has never been demonstrated or even proposed for conventional, electrochemically prepared porous silicon, has several advantages, i.e., it is simple and manufacturable, it allows the use of thick sacrificial layer silicon films, when needed, and it can be used, when desired, to create extremely flat surfaces for the empty region's defining walls, bottom, and top. Alternatively, it can be used, as seen in FIG. 6, to produce channels, tubes, sorting structures, etc. of relatively large cross-section without the need for the so-called deep etch reactive ion etching process. In general, the very effective lift-off processing is possible, even when thick silicon sacrificial films are to be lifted-off (i.e., removed in selected areas), because of the columnar void network morphology of the present film. The unique columnar/void structure allows etching liquids to efficiently reach the stencil (lift-off causing) layer under the columnar void silicon in inter-channel regions. The stencil layer, which defines where the silicon material will be removed, is attacked by chemicals penetrating the columnar void silicon layer. This results in the dissolution or etching away of the stencil layer and the floating away (i.e., the lift-off) of the now unsupported silicon layer in the inter-channel or inter-air gap, etc. regions. The columnar void silicon in what will become the channel regions is not lifted off as seen in FIG. 5 or FIG. 6. The lift-off process results in very flat surfaces in the inter-channel, etc. region, which removes the need for any planarization step and allows one to freely choose the thickness of capping layer of FIG. 5 or 6. Very thin capping layers, if necessary, are thereby permitted. The capping layer is the film, which defines the top (i.e., the roof) of the void structure (e.g., channel, tube, airgap, etc.) as seen in FIG. 4, 5, or 6. A thin capping layer can be a key factor for some applications such as nutrient delivery, drug delivery, and micro-cooler or heater applications because a thick capping layer can impede substance or heat transport to or from a capillary (i.e., channel). In the case of some applications such as fuel cells, the capping layer may actually be composed of a multitude of materials or sublayers some of which may be patterned (e.g., grid-like or screen-like in their pattern). In some applications such as sorting and sensing, the capping layer may be patterned (e.g., grid-like, or screen-like) or a permeable membrane separating the lower void region from another such region above.

IV. Applications

The above discussion outlines several specific applications of the separation technology, of the release layer technology, of the sacrificial layer technology, and combinations of these. In a number of these applications it will be obvious that it is advantageous to create the structures on a laminate on a mother substrate using the present sacrificial layer approach and then to separate this laminate from the mother substrate using the present separation scheme. In all cases, these applications are intended to be suggestive of the flexibility and utility of the approaches of the present invention.

(a) Fuel Cells

This invention demonstrates a novel fabrication process for micro-scale fuel cells based on using the sacrificial layer approach according to the present invention. Fabrication processes that may be used include photolithography, reactive ion etching (RIE), chemical vapor deposition (CVD), selective wet etching, and deep silicon etching. However, the unique feature of the work according to the present invention is its use of large surface to volume ratio material for the sacrificial layer. In this demonstration presented here as an example, the present low-deposition temperature, deposited columnar void network material is used as a sacrificial layer for channel formation. The columnar void network silicon is removed with high etching selectivity to other structure materials to define channels for fuel cell fabrication. Another unique aspect of the present work is its use of lift-off in conjunction with the deposited columnar void network material. Further, in the demonstration, deposited $SiO_2$ material was used as the proton transport medium. Other proton transport materials including Nafion could be utilized. In the demonstration, deposited $Si_3N_4$ was used as a unique proton confinement layer. This application of nitride may or may not be used, depending on the situation.

The advantages of this particular fuel cell design and fabrication include: (1) ease of fabrication, (2) compatibility with lightweight substrates such as plastics and metal foils, (3) ease of combining into stacked structures and ease of integration with transistors, diodes, or both for power management, (4) ease of integration with sensors for chemical reaction control, (5) ease integration with a variety of microfluidics, display pixels, sensors, and detectors for powering various functions, and (6) ease of combining into stacked structures such as those seen in FIG. 3.

FIG. 9a shows a fuel cell structure fabricated on a silicon wafer according to this invention. Here a basic unit of electrode, solid electrolyte and electrode is fabricated on the silicon wafer, in which the channels have been patterned by selective etching of a sacrificial layer. The channels embedded in the silicon substrate play the role of feeding paths for fuels to the fuel cell. The fuel, a hydrogen-bearing source such as hydrogen gas or alcohols like methanol, is fed through the channels for the electron-yielding reaction seen in FIG. 9a. This reaction is the oxidation of hydrogen source to produce protons, electrons and byproducts such as hydrocarbons. The electrode where this occurs is comprised of catalytic materials, such as platinum or palladium. The protons generated by this oxidation reaction diffuse into the proton transport layer toward the opposite electrode. However, the electrons are blocked from entering the proton transport layer because of its low electrical conductivity. Fluorocarbon-polymeric material, for example Nafion™ from DuPont, has been used for the membrane electrolyte for fuel cell for many years and can be the proton transport layer in FIG. 9a. In this invention, other materials, such as deposited silicon dioxide, with its high proton conductivity, can also be used for this solid proton transport layer. The protons penetrate the electrolyte (e.g., Nafion™ or silicon dioxide) toward the other electrode, at which the reduction reaction occurs. This is a reduction of the arriving protons utilizing the electrons that have come through the external electric circuit and oxygen. In FIG. 9a, this oxygen is being supplied from the atmosphere. In other arrangements the oxygen can be arriving through channels in the same manner as the hydrogen. As seen in FIG. 9a, a deposited $Si_3N_4$ layer may be used with the hydrogen source channels to block lateral proton movement. Alternately, this layer may be replaced by deposited $SiO_2$ designed to create a more laterally uniform proton supply.

This fuel cell unit also can be fabricated on other types of substrates such as polymers, glasses, and metal foils. For example, as seen in FIG. 9b, a silicon layer or other material can be deposited on a plastic, glass or metal foil substrate and the fuel cell fabricated in the deposited silicon layer. In this case the sacrificial layer is removed as in FIG. 9a and the removing chemical is used to etch the deposited silicon instead of a wafer material, as necessary.

A detailed process sequence is shown in FIG. 10a and another in FIG. 10b. In FIG. 10a, thick silicon nitride layer is first deposited on a silicon wafer to play the role of defining the channels and of a masking layer for channel etching. In the particular fabrication sequence we have done for the demonstration, electron cyclotron resonance plasma enhanced chemical vapor deposition (ECR-PECVD) processing was used for the silicon nitride deposition although other deposition processes could be used also. The process conditions for silicon nitride deposition are shown in Table 6. In this particular demonstration of this invention, 2500 Å of silicon nitride was deposited using a 15 min deposition. The channel area was defined by photolithography and Magnetically Enhanced Reactive Ion Etching (MERIE) techniques. In this demonstration, 1.3 µm thick photoresist and I-line contact aligner were used for photolithography process. A 30 sec exposure to MERIE etching was carried out to etch 2500 Å of silicon nitride including overetching. The process conditions for MERIE etching of silicon nitride are shown in Table 7. After reactive ion etching of silicon nitride, deposited columnar void network silicon material was deposited for the sacrificial layer. Table 8 shows the details of columnar void network material deposition. As seen, it was deposited on the photoresist and silicon. After this deposition, the columnar void network material on the photoresist was removed by the lift-off procedure discussed in detail above. In the lift-off process, the columnar void network material outside of what will be the channels, is detached by dissolving the underlying photoresist (FIG. 10(a)).

TABLE 6

Deposition Condition for Silicon Nitride using ECR-PECVD

| Item | Details | Condition |
| --- | --- | --- |
| Environment | Temperature | 100° C. |
| | Pressure | 4 mTorr |
| Gases | Ar | 3 sccm |
| | $SiH_4$ | 10 sccm |
| | $N_2$ | 8 sccm |
| Plasma Condition | Upper Magnetic | 173 |
| | Lower Magnetic | 24 |
| | RF Power | 900 Watt |
| Deposition Rate | | 167 Å/min |
| | | (2500 Å @ 15 min) |

TABLE 7

MERIE Process Condition for Silicon Nitride

| Item | Details | Condition |
| --- | --- | --- |
| Environment | Temperature | 25° C. |
| | Pressure | 200 mTorr |
| Gases | $CF_4$ | 45 sccm |
| | $O_2$ | 5 sccm |
| | $N_2$ | 8 sccm |
| Plasma Condition | Magnetic | 50 Gauss |
| | RF Power | 200 Watt |
| Deposition Rate | | 7000 Å/min |
| | | (3500 Å @ 30 sec) |

TABLE 8

Deposition Condition for Columnar void Network Material using ECR-PECVD

| Item | Details | Condition |
| --- | --- | --- |
| Environment | Temperature | 100° C. |
| | Pressure | 8 mTorr |

TABLE 8-continued

Deposition Condition for Columnar void Network Material using ECR-PECVD

| Item | Details | Condition |
| --- | --- | --- |
| Gases | Ar | 2 sccm |
| | $SiH_4$ | 40 sccm |
| Plasma Condition | Upper Magnetic | 173 |
| | Lower Magnetic | 24 |
| | RF Power | 500 Watt |
| Deposition Rate | | 167 Å/min |
| | | (2500 Å @ 15 min) |

After the lift-off process, the catalyst/electrical contact layer aiding proton formation and electron liberation is deposited over the whole surface including the columnar void network silicon material remaining in what will became the channels. In this demonstration, 300 Å of platinum layer was deposited on photoresist by e-gun evaporation. The photoresist was patterned to form a screen-like or grid-like catalyst layer, which resulted in the metal having this pattern after another lift-off process. At this step, this metal is sitting on and is supported by the sacrificial layer. After formation of this electrode, a solid electrolyte was deposited. In the case when silicon dioxide is used for the proton transport medium, an ECR-PECVD process was used for deposition. A spin-coating method was used when Nafion film was employed for the proton transport medium. Table 9 shows the process condition for silicon dioxide deposition using ECR-PECVD. In the demonstration using Nafion, the coating procedure was carried out for 30~50 sec with the spin speed of 500~4000 rpm, depending the target thickness.

TABLE 9

Deposition Condition for Silicon Dioxide using ECR-PECVD

| Item | Details | Condition |
| --- | --- | --- |
| Environment | Temperature | 100° C. |
| | Pressure | 4 mTorr |
| Gases | $SiH_4$ | 4 sccm |
| | $O_2$ | 5.1 sccm |
| | Ar | 3 sccm |
| Plasma Condition | Upper Magnetic | 173 |
| | Lower Magnetic | 24 |
| | RF Power | 900 Watt |
| Deposition Rate | | 130 Å/min |
| | | (3900 Å @ 30 min) |

At this point through-holes were created to provide access to the sacrificial columnar void network material. These were patterned by selectively etching the solid proton transport medium. In the case of silicon dioxide, BOE (Buffered Oxide Etchant 10:1 $NH_4F$:HF) is used to selectively etch the oxide with the etching rate of 14600 Å/min at 21° C. After through-hole etching, the channel was opened by the selective etching of columnar void network material and the substrate silicon in an etching solution, such as TMAH (Tetra-Methyl Ammonium Hydroxide), $NH_4OH$ solution. The columnar void network material layer plays the role of a blotter allowing easy and uniform access by the etchant. This columnar void network material has a high etching rate at TMAH solution. The etchant is also able to uniformly attack the silicon layer as seen in part d of FIG. 10a. This is a very uniform etch of the underlying silicon (which may be wafer material or deposited Si) since the columnar void network material acts a s a blotter and then very uniformly exposes the underlying Si to etching.

Of course, these blotting and etchant-source functions of the columnar void material can be adjusted by adjusting film porosity and through-hole positioning and size. In this demonstration, a 20 min etching in 5% TMAH solution at 75° C. resulted in 1520 µm deep-channels in the silicon substrate. The channels fabricated by this etching allow fuel supply after completion of fuel cell fabrication (FIG. 10a, part 5).

Figure 3:
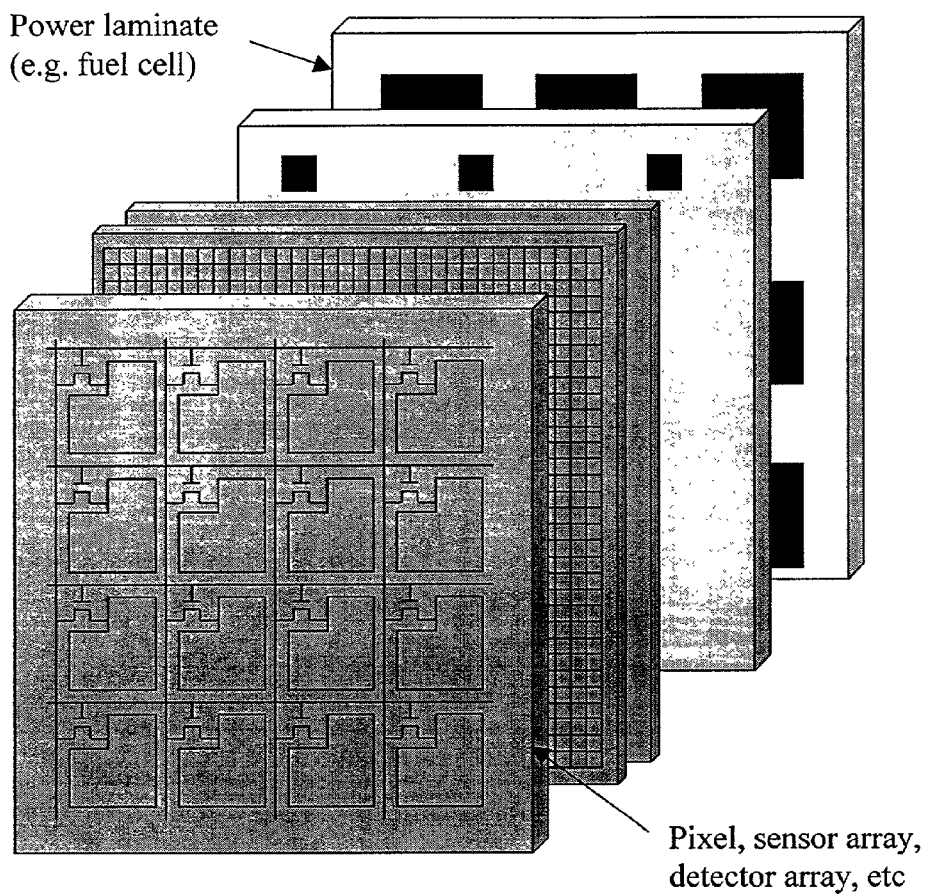
FIG. 3 depicts a CAPS structure which is made up of several plastic laminates containing circuits and power devices such as fuel cells. In this example the final laminate contains pixels making the system into a display. The individual laminates that have been assembled to make this system have each been fabricated and separated following methodologies outlined in FIG. 1 or 2.

When the substrate is a [100]-oriented silicon wafer, the channel shapes can be that seen in FIG. 10a, parts 4 and 5. When the substrate is silicon or other material deposited on a coated or uncoated mechanical substrate such as glass, plastic, metal foil, or other material, the channel shape will be that seen in FIG. 10b, parts 4 and 5. The overhanging layer ($Si_3N_4$ in FIG. 10b) mechanically supports the grid and solid electrolyte. When $Si_3N_4$ is used, it also blocks communication among channels. When this processing is done with this silicon or other material formed in or on a laminate on a mother substrate, the laminate can be separated as outlined and used as seen in FIGS. 1, 2 and 3.

Depending on the position of the through-holes, after channel formation, additional deposition of solid proton electrolyte may be needed to cover the entire surface with electrolyte material. In any case, after filling the through-hole, the top (reduction grid) layer is deposited on the top of electrolyte and patterned with the same method of patterning used for the other electrode.

The micro-scale fuel cell fabricated with this invention has a broad range of applications. In addition, the size of fuel cells produced by this approach outlined here can be reduced to make the cell as small as is needed by the specific application. Current technology is easily capable of defining patterns below hundred nanometers. In this size regime, the channel can be defined as "nano-channel".

A typical PEM fuel cell comprises one or more layered films and separators alternatively stacked with each other. This layered sandwich consists of a polymer electrode membrane (PEM), an anode and a cathode, with the PEM film interposed between two electrodes.

Such small fuel cells, which can show better efficiency than the usual conventional macro-scale fuel cells, can be on-site power generators in integrated structures with MEMS devices, displays, sensor arrays, detector arrays, and multifunction systems all on the same substrate. In addition, using the processing techniques outlined here, fuel cells can be stacked onto each other to generate higher voltages or can be connected in parallel to generate higher currents, as preferred. Further, these cells can be fabricated on plastic or other types of laminates and integrated into systems as shown in the CAPS concept of FIG. 3. Fuel cells are a promising means for a portable power in mobile electronics due to their lightweight and high energy density. Applications in portable power uses include the full range of consumer electronics, such as cell phones, laptop/palmtop computers, video camcorders, and so on. Integrating the micro-scale fuel cell approach onto lightweight substrate such as plastics, glasses, and foils will allow the powering of light weight displays, sensor and detector structures, telecommunications, and systems incorporating these and other functions.

(b) Smart Power

The fuel cell structures discussed above can be fabricated with transistors, diodes, or both integrated into the fuel cell layout. With the presence of such electronics, circuits can be integrated with the fuel cell structures to give a smart power laminate. This smart power would on-demand couple fuel cells in the laminate together in parallel or series, or variations thereof to give the instantaneous current, voltage, and power needed in an application. Sensors, detectors, and MEMs devices can also be incorporated into such systems to allow chemical reaction control and fuel diversion and consumption control.

(c) Displays

The cavities and channels that can be created by the sacrificial layer approach can be used in display applications. For example, these structures can be created with electrodes in the enveloping layers. They can accommodate field emission sources or be filled with gases selected such that, when voltages are impressed on these electrodes, the gases ionize forming a light emitting plasma. Hence individual cavities or channels can be used as pixels, separately controlled, to form plasma color displays. Control can be built into or on the material in which the cavities or channels have been built. If transistors or diodes are used for this control, active matrix plasma displays can be built. Obviously, this can be accomplished on laminates which are then separated from the mother substrate using also the separation methodology. Such display laminates can be part of the systems shown in FIG. 3, if desired.

(d) Sorting and Sensor Structures

Figure 11:
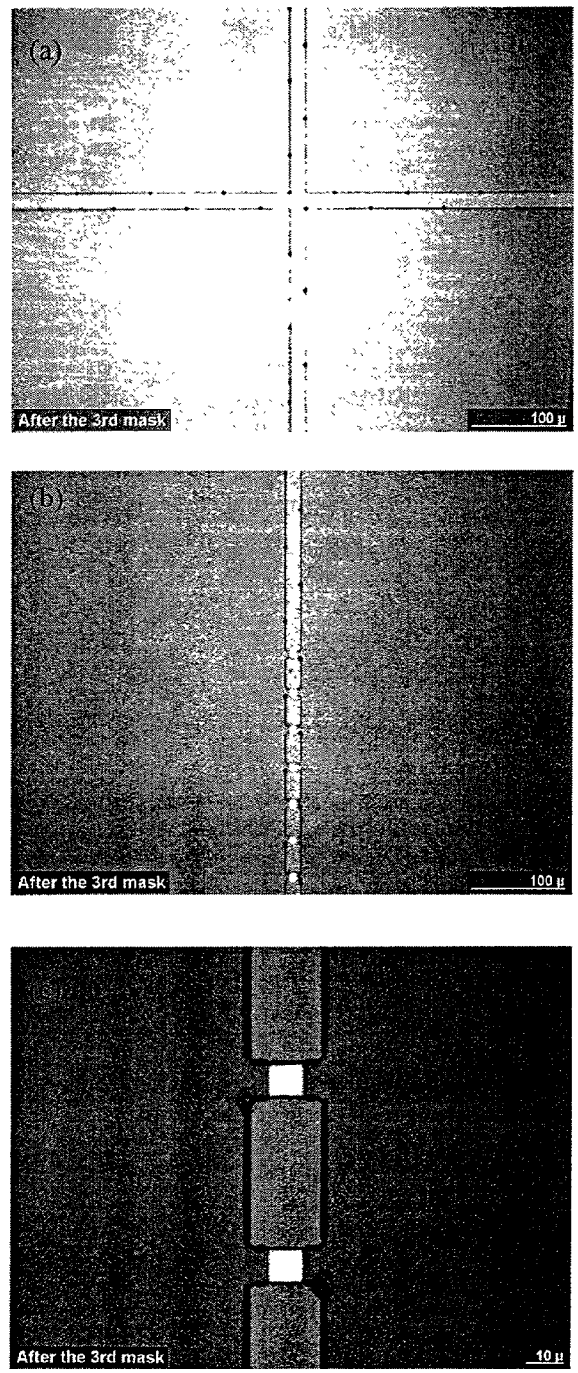
FIGS. 11a-c are pictures of an actual sorting structure formed using the columnar void layer as the sacrificial material. Such a structure could be on a laminate formed by the separation procedure.

Using the sacrificial materials and methodologies disclosed in this invention, sorting, filtering, and sensor structures can be fabricated even on plastic, glass, or metal foils. Combining these procedures with the separation layer methodologies, means such structures can be formed in and on materials on mother substrates and then separated for use in systems such as in the concept of FIG. 3. Combining these structures with active circuit elements in and on the same materials means these structures can be adaptive and smart. FIG. 11 shows an actual DNA sorting structure fabricated using the sacrificial layer materials, design, and fabrication methodology outlined earlier.

Figure 12:
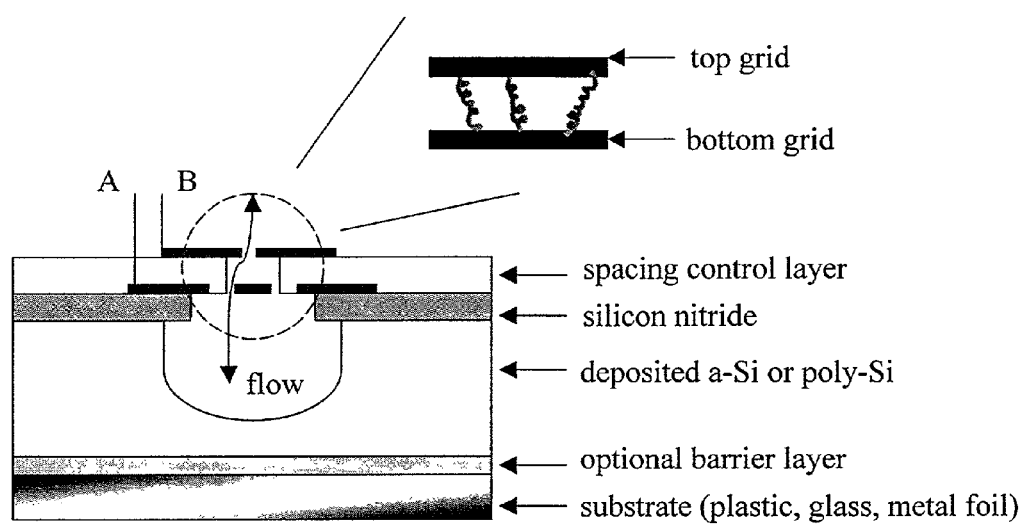
FIG. 12 illustrates a molecular immobilization for detection. Detection can be accomplished by monitoring the ac or dc electrical response between the electrodes immobilizing the molecular entity.

Structures with channels or even the varying cross-sections of FIG. 11 can have electrodes or conductive grids incorporated into the enveloping cavity walls, ceiling, or floor. With careful control of electrode or grid spacing, as is possible with the deposited sacrificial layers, these spacings can accommodate molecular units. With the proper choice of self-assembling molecules and electrode and grid materials, molecules can be selected for attachment across these spacings. The molecules can be selected for detection and sensing. For example, single strand DNA can be attached in these channels such as those of FIG. 11 and used to detect incoming DNA samples. Detection, for example, could be attained by a change of conductivity between electrodes. Such detection can be attained for other entities by selection of the molecules immobilized between electrodes. The general scheme is seen in FIG. 12.

(e) Release Structures

Our column void network material is very effective as a release material. Release layers are commonly used in many MEMS devices to form structures connected in at least one place to another materials system. An excellent example of release layer applications is the creation of a cantilever structure. Our materials are excellent for release layer applications because they have high etch rate and etch selectivity over commonly used structural layers such as silicon nitride and silicon oxide. In fact, the etch rate of the columnar void network film, 2.5 µm/min, is about four times faster than that of poly silicon, 0.6 µm/min, and poly-Si is one of the most commonly used release materials. In addition, the fast etch rate of the film reduces chemical exposing time of structural layers, and it increases overall process reliability. FIG. 13 shows micro-switch structure as an example of a release layer utilization in fabrication.

It should be understood that the foregoing description is only illustrative of the present invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method for processing a substrate comprising the steps of:
   depositing a layer of high surface area to volume ratio material having a non-helical columnar structure over a surface of said substrate;
   removing at least a portion of said high surface area to volume ratio material layer;
   depositing a stencil layer on said substrate; and
   patterning said stencil layer and selectively removing a portion of said stencil layer, thereby leaving an exposed portion of said substrate and at least one retained portion of said stencil layer,
   wherein the step of depositing a layer of high surface area to volume ratio material comprises depositing said high surface area to volume ratio material upon said exposed surface of said substrate and on said at least one retained portion of said stencil layer, further comprising the step of lifting off said stencil layer, thereby also removing a portion of said high surface area to volume ratio material layer deposited thereon.

2. The method of claim 1, further comprising the step of depositing a second layer over said substrate and said high surface area to volume ratio material layer.

3. The method of claim 2, further comprising the step of creating through-holes through said second layer for the removal of said high surface to volume ratio material layer through said created through-holes to produce a cavity structure.

4. The method of claim 3, after removal of said high surface area to volume ratio material layer through said created through-holes to produce a cavity structure, thereafter further comprising the step of depositing a layer that blocks said through-holes.

5. The method of claim 3, after removal of said columnar void layer through said created through-holes to produce a cavity structure, thereafter further comprising the steps of adding a gas or liquid in said cavity structure; and depositing a layer that blocks said through-holes and seals said cavity structure.

6. The method of creating a cavity structure in a substrate comprising:
   a. forming at least one stencil layer over a substrate;
   b. removing a portion of said stencil layer thereby created an exposed portion of said substrate;
   c. forming a high surface area to volume ratio material layer over said portion of said stencil layer and said exposed substrate;
   d. lifting off a portion of said stencil layer, thereby also removing a portion of said high surface area to volume ratio material layer formed thereover and leaving the portion of said high surface area to volume ratio material layer formed on said exposed substrate;
   e. forming at least one layer over said substrate and said high surface area to volume ratio material layer; and
   f. removing said high surface area to volume ratio material layer to form a cavity structure.

7. The method of claim 6, wherein said stencil layer comprises a material selected from the group consisting of photoresists, nitrides, oxides, metals, polymers, dielectrics and combinations thereof.

8. The method of claim 6, wherein said substrate is selected from the group consisting of silicon wafers, quartz, glass, organic materials, polymers, ceramics, semiconductor, metals, insulators, and combinations thereof.

9. The method of claim 6, whereby removing said stencil layer in step (b) is performed using a technique selected from a group consisting of dissolving, dry etching, wet etching and combinations thereof.

10. The method of claim 6, wherein said high surface area to volume ratio material layer is deposited.

11. The method of claim 6, wherein said high surface area to volume ratio material is a columnar void layer.

12. The method of claim 11, wherein said columnar void layer is a nano-scale composition comprising:
    (a) a plurality of uniform essentially non-contacting basic columnar-like units penetrating a continuous void wherein said units have adjustable regular spacing, adjustable uniform height, and adjustable variable diameter, and
    (b) said plurality of basic columnar-like units are uniformly orientated and disposed over said substrate.

13. The method of claim 6, wherein lifting off said stencil layer in step (d) is performed by dissolving, etching or combinations thereof.

14. The method of claim 6, wherein said at least one layer is a material selected from the group consisting of chemically active materials, polymers, insulators, nitrides, oxides, piezoelectrics, ferroelectrics, metals, pyroelectrics, biological materials and semiconductors.

15. The method of claim 6, wherein removing the high surface area to volume ratio material layer in step (f) is performed by chemical means, mechanical means or combinations thereof.

16. The method of claim 6, further comprising the step of creating through-holes to access said high surface area to volume ratio material layer.

17. The method of claim 6, further comprising the step of adding gas or liquid into said cavity structure after said high surface area to volume ratio material layer is removed in step (f).

18. The method of claim 16, further comprising the step of depositing a further layer, wherein said further layer blocks said through-holes.

19. The method of claim 18, wherein said further layer is a material selected from the group consisting of dielectric, polymeric, metal, photoresist, nitride, oxide, biological, semiconductor, and insulator materials and combinations thereof.

20. The method of claim 6, wherein said cavity structure has a height of at least about 10 nm.

21. The method of claim 6, wherein said cavity structure has a width of at least about 10 nm.

22. The method of claim 6, wherein formation of said cavity structure provides for the fabrication of a use selected from the group consisting of MEMS; field emission sources; bolometric structures; accelerometers; light trapping; resonance; field shaping; transmission; acoustic trapping; display micro-mirror formations; biomedical and medical devices; sorting structures for functions such as DNA and proteomic sorting; cell nutrition, growth control, or both; capillary functions; gettering regions for solid phase crystallization or silicon on insulator structures; interlayer stress control; optical waveguide and optical device applications; fluid channels for electrical, chemical, and electrochemical sensors, chromatography, chemical reactant/product transport; fuel cells; display, and molecular sorting.

23. A method of producing at least one contact region between a first and a second material system over a substrate comprising the steps of:
   a. forming a first material system over said substrate;
   b. etching a portion of said first material system;
   c. forming high surface area to volume ratio material layer over said first material system and said substrate;
   d. removing a portion of said high surface area to volume ratio material layer to expose a portion of said first material system;
   e. forming a second material system over said high surface area to volume ratio material layer and exposed portions of said first material system, so that a portion of said second material system contacts a portion of said first material system; and
   f. removing said high surface area to volume ratio material layer, thereby freeing a portion between said first and second material systems while maintaining said at least one contact region.

24. The method of claim 23, wherein said first material system is selected from the group consisting of metals, semiconductors, chemically active materials, polymers, insulators, nitrides, oxides, piezoelectrics, ferroelectrics, pyroelectrics, biological materials, organic materials and combinations thereof.

25. The method of claim 23, wherein said substrate is a material selected from the group consisting of silicon wafers, quartz, glass, organic materials, polymers, ceramics, semiconductor, metals, and combinations thereof.

26. The method of claim 23, wherein said second material system is selected from the group consisting of metals, semiconductors, chemically active materials, polymers, insulators, nitrides, oxides, piezoelectrics, ferroelectrics, pyroelectrics, biological materials, organic materials, and combinations thereof.

27. The method of claim 23, wherein removal of said high surface area to volume ratio material layer is facilitated by chemical means, physical means or combination thereof.

28. The method of claim 27, wherein removal of said high surface area to volume ratio material layer by chemical means has an etch rate of 25 µm per minute or less.

29. The method of claim 23, wherein production of at least one contact region between a first and a second material system provides for fabrication of a structure selected from the group consisting of MEMS devices, cantilever structures, micro-switch structures, micro-mirror structure, actuators, field emission structures, bolometric structures, accelerometers, biomedical and medical devices, sorting and affixing structures, and electrical, chemical, and electrochemical sensors.

* * * * *